(12) United States Patent
Sato et al.

(10) Patent No.: US 9,255,855 B2
(45) Date of Patent: Feb. 9, 2016

(54) TORQUE MEASUREMENT APPARATUS, METHOD, AND PROGRAM

(71) Applicant: PANASONIC INTELLECTUAL PROPERTY MANAGEMENT CO., LTD., Osaka (JP)

(72) Inventors: Taichi Sato, Kyoto (JP); Yuko Tsusaka, Osaka (JP); Yudai Fudaba, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 45 days.

(21) Appl. No.: 14/164,710

(22) Filed: Jan. 27, 2014

(65) Prior Publication Data

US 2014/0137669 A1 May 22, 2014

Related U.S. Application Data

(63) Continuation of application No. PCT/JP2013/003493, filed on Jun. 3, 2013.

(30) Foreign Application Priority Data

Jun. 7, 2012 (JP) ................................. 2012-129564

(51) Int. Cl.
*G01L 3/04* (2006.01)
*A61B 6/12* (2006.01)
(Continued)

(52) U.S. Cl.
CPC . *G01L 3/04* (2013.01); *A61B 6/022* (2013.01); *A61B 6/12* (2013.01); *A61B 6/4014* (2013.01); *G01L 3/12* (2013.01); *A61M 25/0108* (2013.01); *A61M 25/0113* (2013.01)

(58) Field of Classification Search
CPC ........ A61B 6/4014; A61B 6/022; A61B 6/12; G01L 3/04; G01L 3/12; A61M 25/0113; A61M 25/0108

USPC .................................................... 73/862.321
See application file for complete search history.

(56) References Cited

U.S. PATENT DOCUMENTS

2006/0018426 A1* 1/2006 Bruder et al. ................... 378/19
2007/0291894 A1* 12/2007 Hagiwara et al. ................ 378/4
(Continued)

FOREIGN PATENT DOCUMENTS

| JP | 60-217326 | * 10/1985 |
| JP | 3-295534 | * 12/1991 |

(Continued)

OTHER PUBLICATIONS

International Search Report issued Jul. 2, 2013 in International (PCT) Application No. PCT/JP2013/003493.*
(Continued)

*Primary Examiner* — Lisa Caputo
*Assistant Examiner* — Philip Cotey
(74) *Attorney, Agent, or Firm* — Wenderoth, Lind & Ponack, L.L.P.

(57) ABSTRACT

A first angle acquiring unit acquires a rotational angle of a characteristic portion in a predetermined region on an inlet side of an insertion member of a linear body extending through the insertion member. From an image of the linear body inserted into a body of a subject, a second angle acquiring unit acquires a direction of a curved portion of the linear body inserted into the body of the subject and then acquires a rotational angle of a distal end of the linear body. A torque calculation unit calculates a torque based on a difference between the rotational angle in the predetermined region acquired by the first angle acquiring unit and the rotational angle of the distal end of the linear body acquired by the second angle acquiring unit.

8 Claims, 28 Drawing Sheets

(51) Int. Cl.
   *G01L 3/12*   (2006.01)
   *A61B 6/02*   (2006.01)
   *A61B 6/00*   (2006.01)
   *A61M 25/01*  (2006.01)

(56) References Cited

U.S. PATENT DOCUMENTS

| | | | |
|---|---|---|---|
| 2008/0097404 A1* | 4/2008 | Yribarren et al. | 604/529 |
| 2008/0231264 A1* | 9/2008 | Krueger | G01D 5/208 324/207.22 |
| 2010/0292566 A1* | 11/2010 | Nagano et al. | 600/424 |
| 2011/0103550 A1* | 5/2011 | Proksa | 378/63 |
| 2011/0234780 A1* | 9/2011 | Ito | A61B 1/2676 348/65 |
| 2012/0275645 A1* | 11/2012 | Koenig et al. | 382/103 |
| 2013/0201311 A1* | 8/2013 | Hirakawa | 348/74 |

FOREIGN PATENT DOCUMENTS

| | | | |
|---|---|---|---|
| JP | 6-221942 | * | 8/1994 |
| JP | 8-71035 | * | 3/1996 |
| JP | 2000-10467 | * | 1/2000 |
| JP | 2001-80765 | * | 3/2001 |
| JP | 2009-502396 | * | 1/2009 |
| JP | 2009-279343 | * | 12/2009 |
| JP | 2009-279344 | * | 12/2009 |
| JP | 4728456 | * | 7/2011 |

OTHER PUBLICATIONS

International Preliminary Report on Patentability and Written Opinion of the International Searching Authority issued Dec. 18, 2014 in International (PCT) Application No. PCT/JP2013/003493.

* cited by examiner

| IDENTIFIER | ANGLE INFORMATION (RADIAN) |
|---|---|
| 0 | 0.28975 |
| 1 | −0.4429 |

Fig.12
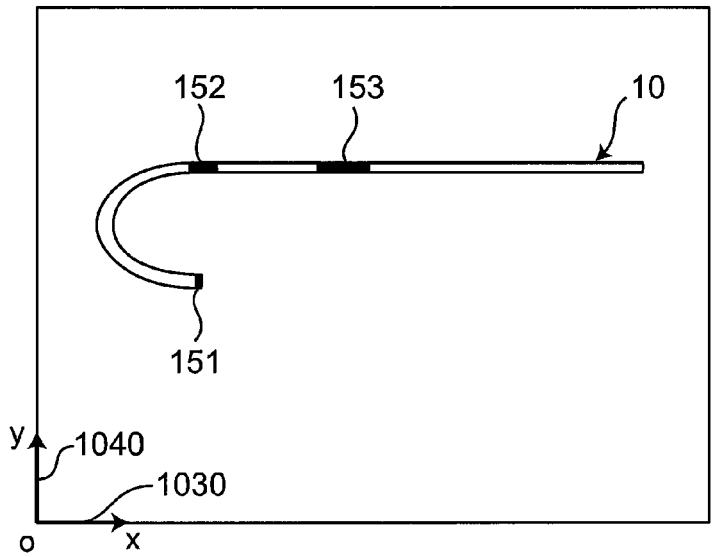
Fig.13
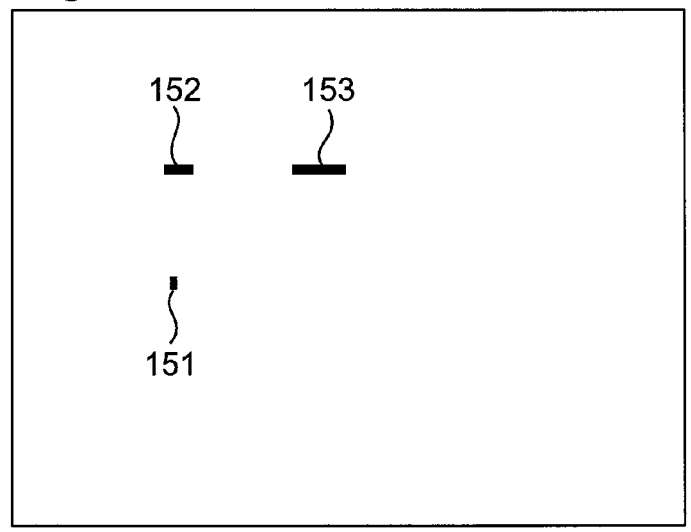
Fig.14
| IMAGE NUMBER | CHARACTERISTIC POINT | x(PIXEL) | y(PIXEL) |
|---|---|---|---|
| 0 | 0 | 100 | 125 |
|   | 1 | 100 | 175 |
|   | 2 | 150 | 175 |
| 1 | 0 | 100 | 110 |
|   | 1 | 100 | 130 |
|   | 2 | 150 | 130 |

| CHARACTERISTIC POINT | X | Y | Z |
|---|---|---|---|
| 0 | 700.5 | 100.3 | 200.2 |
| 1 | 700.5 | 100.3 | 202.1 |
| 2 | 710.2 | 100.3 | 202.1 |

| VECTOR | X(mm) | Y(mm) | Z(mm) |
|---|---|---|---|
| 0 | 9.7 | 0 | 0 |
| 1 | 0 | 0 | −1.9 |

| TORQUE (N·m) | 1.00 |
|---|---|

Fig.27

| L | f(L) |
|---|---|
| 0 | 0 |
| 1 | $\dfrac{1}{G_1 \times J_1}$ |
| 2 | $\dfrac{2}{G_1 \times J_1}$ |
| 3 | $\dfrac{3}{G_1 \times J_1}$ |
| 4 | $\dfrac{4}{G_1 \times J_1}$ |
| 5 | $\dfrac{5}{G_1 \times J_1}$ |
| 6 | $\dfrac{6}{G_2 \times J_2} + \dfrac{G_2 \times J_2 - G_1 \times J_1}{G_1 \times J_1 \times G_2 \times J_2} \times 5$ |
| 7 | $\dfrac{7}{G_2 \times J_2} + \dfrac{G_2 \times J_2 - G_1 \times J_1}{G_1 \times J_1 \times G_2 \times J_2} \times 5$ |
| ... | ... |
| 50 | $\dfrac{50}{G_2 \times J_2} + \dfrac{G_2 \times J_2 - G_1 \times J_1}{G_1 \times J_1 \times G_2 \times J_2} \times 5$ |
| ... | ... |
| 300 | $\dfrac{300}{G_2 \times J_2} + \dfrac{G_2 \times J_2 - G_1 \times J_1}{G_1 \times J_1 \times G_2 \times J_2} \times 5$ |

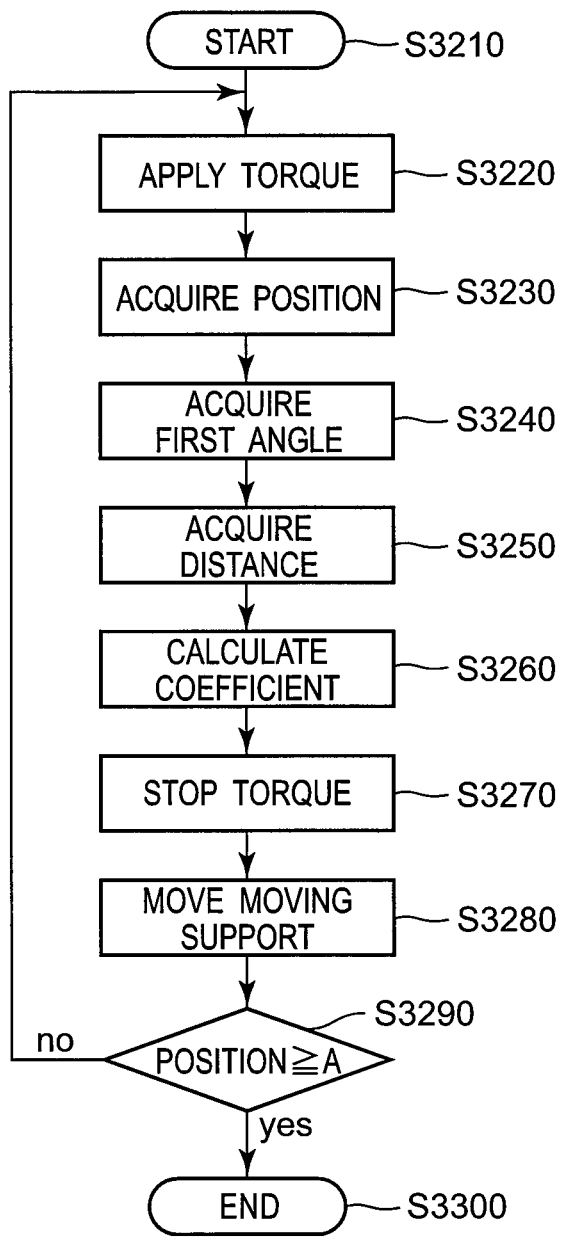

TORQUE MEASUREMENT APPARATUS, METHOD, AND PROGRAM

CROSS-REFERENCE TO RELATED APPLICATIONS

This is a continuation application of International Application No. PCT/JP2013/003493, with an international filing date of Jun. 3, 2013, which claims priority of Japanese Patent Application No.: 2012-129564 filed on Jun. 7, 2012, the content of which is incorporated herein by reference.

TECHNICAL FIELD

The technical field relates to an apparatus, method, and program measuring a torque applied to a flexible linear body.

BACKGROUND ART

Patent Literature 1 describes a device which detects a curving amount of a linear body 9006. The device in Patent Literature 1 has, in the linear body 9006, a unit which obtains a collapsed condition of the linear body 9006. Therefore, its manufacturing cost becomes higher.

In addition, Patent Literature 1 describes insertion length detection means which measures an insertion length of the linear body 9006. As shown in FIG. 29, marks 9021 are provided at predetermined intervals on a surface of the linear body 9006 in Patent Literature 1. A sensor 9022 counts the number of passed marks 9021 to acquire the length of the linear body 9006 inserted into a body of a patient based on the number of passed marks 9021. The insertion length detection means measures the length of the linear body 9006 which has passed before the sensor 9022, but does not measure a distance between two points of the linear body 9006.

CITATION LIST

Patent Literature

Patent Literature: Japanese Unexamined Patent Publication No. 3-295534

SUMMARY OF THE INVENTION

One non-limiting and exemplary embodiment provides a torque measurement apparatus, method, and program acquiring a magnitude of a torque applied to a flexible linear body, which has been difficult.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: a torque measurement apparatus for, when a linear body which has a linear characteristic portion in parallel with an axial direction thereof, is flexible, and has a curved portion at a distal end thereof is inserted through an insertion member into a body of a subject, measuring a torque applied to the linear body, the apparatus comprising:

a first angle acquiring unit which acquires a rotational angle of the characteristic portion in a predetermined region on an inlet side of the insertion member of the linear body extending through the insertion member;

a second angle acquiring unit which acquires a direction of the curved portion of the linear body inserted into the body of the subject from an image of the linear body inserted into the body of the subject, and then, acquires a rotational angle of the distal end of the linear body; and a torque calculation unit which calculates the torque based on a difference between the rotational angle in the predetermined region acquired by the first angle acquiring unit and the rotational angle of the distal end of the linear body acquired by the second angle acquiring unit, wherein the linear body includes a first portion located on a distal end side and formed of a first material and a second portion connected to the first portion and formed of a second material having hardness different from the first material, the first angle acquiring unit acquires a rotational angle of the characteristic portion of the second portion in the predetermined region on the inlet side of the insert ion member of the linear body extending through the insertion member, from an image of the linear body inserted into the body of the subject, the second angle acquiring unit acquires a rotational angle of the first portion of the linear body inserted into the body of the subject, and the torque calculation unit calculates the torque based on a difference between the rotational angle of the second portion of the linear body acquired by the first angle acquiring unit and the rotational angle of the first portion of the linear body acquired by the second angle acquiring unit.

These general and specific aspects may be implemented using a system, a method, and a computer program, and any combination of systems, methods, and computer programs.

According to the aspect of the present disclosure, the magnitude of the torque applied to the flexible linear body can be acquired.

BRIEF DESCRIPTION OF DRAWINGS

These and other aspects and features of the present disclosure will become clear from the following description taken in conjunction with the embodiments thereof with reference to the accompanying drawings, in which:

FIG. 12 is a view showing a transparent image according to the first embodiment;

FIG. 13 is a view showing a binary image of the transparent image according to the first embodiment;

FIG. 14 is a table-form view showing an example of a data structure of a position holding unit according to the first embodiment;

FIG. 27 is a table form view showing a data structure held by a third coefficient holding unit according to the first modification example of the second embodiment;

FIG. 33 is a flowchart showing a flow of a coefficient acquiring process performed by the coefficient acquiring device of the second modification example.

DETAILED DESCRIPTION

Figure 1:
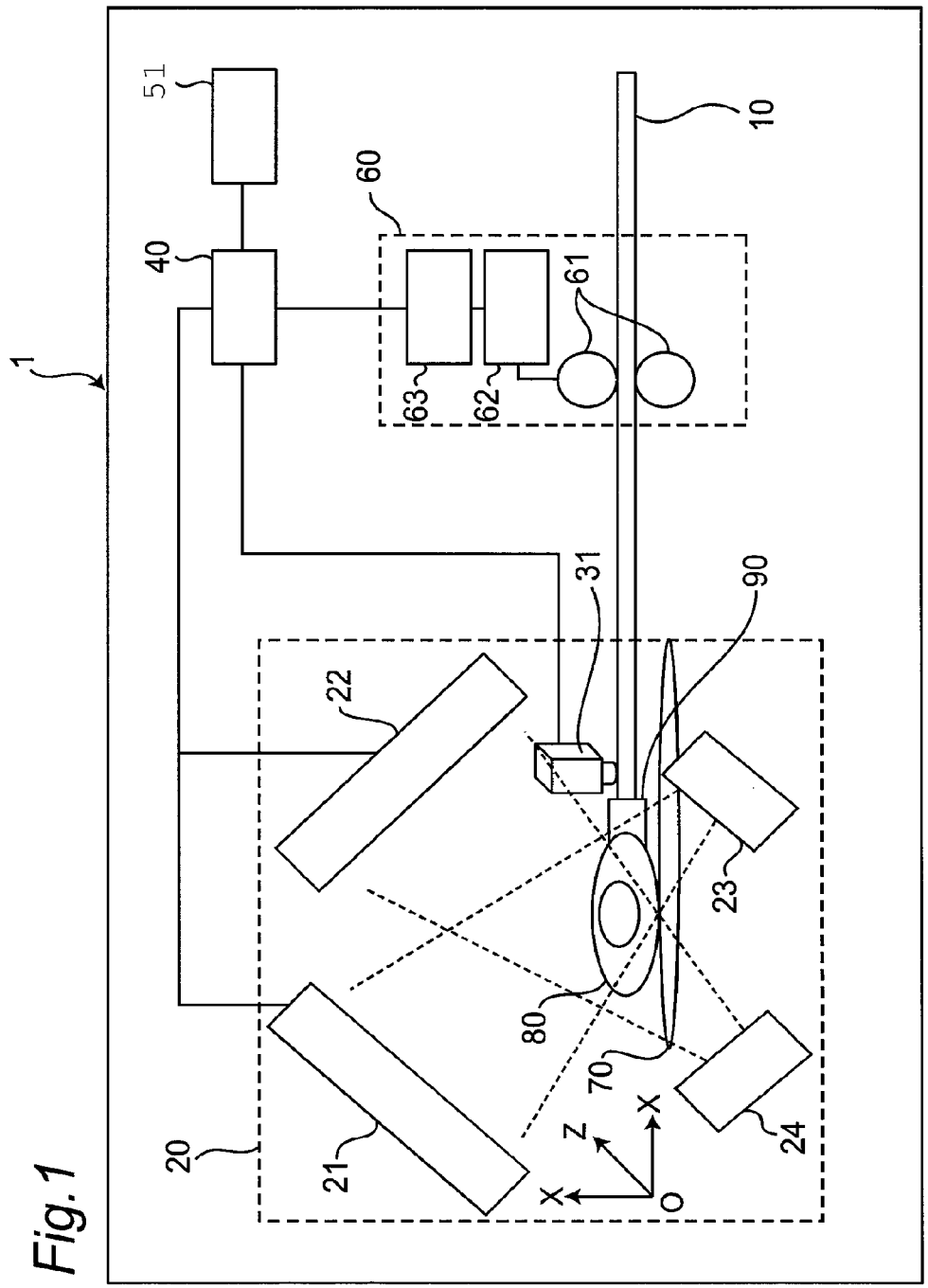
FIG. 1 is a view showing a configuration of a torque measurement apparatus according to a first embodiment.

Referring now to the accompanied drawings the embodiments of the present disclosure will be described in detail below.

Examples of the disclosed technique are as follows.

1st aspect: a torque measurement apparatus for, when a linear body which has a linear characteristic portion in parallel with an axial direction thereof, is flexible, and has a curved portion at a distal end thereof is inserted through an insertion member into a body of a subject, measuring a torque applied to the linear body, the apparatus comprising:

a first angle acquiring unit which acquires a rotational angle of the characteristic portion in a predetermined region on an inlet side of the insertion member of the linear body extending through the insertion member;

a second angle acquiring unit which acquires a direction of the curved portion of the linear body inserted into the body of the subject from an image of the linear body inserted into the body of the subject, and then, acquires a rotational angle of the distal end of the linear body; and a torque calculation unit which calculates the torque based on a difference between the rotational angle in the predetermined region acquired by the first angle acquiring unit and the rotational angle of the distal end of the linear body acquired by the second angle acquiring unit, wherein the linear body includes a first portion located on a distal end side and formed of a first material and a second portion connected to the first portion and formed of a second material having hardness different from the first material, the first angle acquiring unit acquires a rotational angle of the characteristic portion of the second portion in the predetermined region on the inlet side of the insertion member of the linear body extending through the insertion member, from an image of the linear body inserted into the body of the subject, the second angle acquiring unit acquires a rotational angle of the first portion of the linear body inserted into the body of the subject, and the torque calculation unit calculates the torque based on a difference between the rotational angle of the second portion of the linear body acquired by the first angle acquiring unit and the rotational angle of the first portion of the linear body acquired by the second angle acquiring unit.

2nd aspect: a torque measurement apparatus for, when a linear body which has a linear characteristic portion in parallel with an axial direction thereof, is flexible, and has a curved portion at a distal end thereof is inserted through an insertion member into a body of a subject, measuring a torque applied to the linear body, the apparatus comprising:

a first angle acquiring unit which acquires a rotational angle of the characteristic portion in a predetermined region on an inlet side of the insertion member of the linear body extending through the insertion member;

a second angle acquiring unit which acquires a direction of the curved portion of the linear body inserted into the body of the subject from an image of the linear body inserted into the body of the subject, and then, acquires a rotational angle of the distal end of the linear body; and a torque calculation unit which calculates the torque based on a difference between the rotational angle in the predetermined region acquired by the first angle acquiring unit and the rotational angle of the distal end of the linear body acquired by the second angle acquiring unit, wherein the linear body includes a first portion located on an distal end side and formed of a first material and a second portion connected to the first portion and formed of a second material harder than the first material, the first angle acquiring unit acquires a rotational angle of the characteristic portion of the second portion in the predetermined region on the inlet side of the insertion member of the linear body extending through the insertion member, from an image of the linear body inserted into the body of the subject, the second angle acquiring unit acquires a rotational angle of the first portion of the linear body inserted into the body of the subject, and the torque calculation unit calculates the torque based on a difference between the rotational angle of the second portion of the linear body acquired by the first angle acquiring unit and the rotational angle of the first portion of the linear body acquired by the second angle acquiring unit.

According to the 1st and 2nd aspects, a magnitude of the torque applied to the flexible linear body can be acquired. In addition, even when the flexible linear body is made of a plurality of materials, the magnitude of the torque applied to the linear body can be acquired.

3rd aspect: the torque measurement apparatus according to the 1st aspect, further comprising a coefficient acquiring device which acquires a proportional coefficient of the linear body based on difference between the materials of the linear body, wherein the torque calculation unit calculates the torque in consideration of information on a relation between the coefficient which is previously created based on the coefficient acquired by the coefficient acquiring device and a position of the linear body.

According to the 3rd aspect, a proportional coefficient of a linear body having an unknown proportional coefficient can be acquired.

4th aspect: the torque measurement apparatus according to any one of the 1st to 3rd aspects, further comprising a transparent image acquiring unit which images a transparent image of the linear body inserted into the body of the subject, wherein from the transparent image acquired by the transparent image acquiring unit, the second angle acquiring unit acquires the direction of the curved portion of the linear body inserted into the body of the subject to acquire the rotational angle of the distal end of the linear body.

According to the 4th aspect, a magnitude of the torque applied to the flexible linear body can be acquired.

5th aspect: the torque measurement apparatus according to anyone of the 1st to 4th aspects, further comprising:

a camera which images the predetermined region on the inlet side of the insertion member of the linear body extending through the insertion member; and a position acquiring unit which acquires a position of the characteristic portion in the predetermined region based on the image imaged by the camera, wherein the first angle acquiring unit acquires the rotational angle of the characteristic portion in the predetermined region based on the position of the characteristic portion in the predetermined region acquired by the position acquiring unit.

According to the 5th aspect, a magnitude of the torque applied to the flexible linear body can be acquired.

6th aspect: the torque measurement apparatus according to any one of the 1st to 5th aspects, further comprising:

a decision unit which decides whether or not the torque acquired by the torque calculation unit is larger than a predetermined value; and an output unit which outputs an alarm when the decision unit decides that the torque is larger than the predetermined value.

According to the sixth aspect, when the magnitude of the torque applied to the flexible linear body is larger than the predetermined value, an operator receives the alarm and can manipulate so that the torque is not to be larger than that.

7th aspect: a torque measurement method of, when a linear body which has a linear characteristic portion in parallel with an axial direction thereof, is flexible, and has a curved portion at a distal end thereof is inserted through an insertion member into a body of a subject, measuring a torque applied to the linear body, the method comprising:

when the linear body includes a first portion located on a distal end side and formed of a first material and a second portion connected to the first portion and formed of a second material having hardness different from the first material, acquiring a rotational angle of the characteristic portion of the second portion in a predetermined region on an inlet side of the insertion member of the linear body extending through the insertion member by using a first angle acquiring unit;

acquiring a direction of the first portion of the linear body inserted into the body of the subject from an image of the linear body inserted into the body of the subject, and then, acquiring a rotational angle of the first portion of the linear body, by using a second angle acquiring unit; and calculating the torque based on a difference between the rotational angle of the second portion of the linear body acquired by the first angle acquiring unit and the rotational angle of the first portion of the linear body acquired by the second angle acquiring unit by using a torque calculation unit.

According to the 7th aspect, a magnitude of the torque applied to the flexible linear body can be acquired. In addition, even when the flexible linear body is made of a plurality of materials, the magnitude of the torque applied to the linear body can be acquired.

8th aspect: a computer-readable recording medium including a torque measurement program of, when a linear body which has a linear characteristic portion in parallel with an axial direction thereof, is flexible, and has a curved portion at a distal end thereof is inserted through an insertion member into a body of a subject, measuring a torque applied to the linear body, the program which has a computer execute:

when the linear body includes a first portion located on a distal end side and formed of a first material and a second portion connected to the first portion and formed of a second material having hardness different from the first material, a first angle acquiring step of acquiring a rotational angle of the characteristic portion of the second portion in a predetermined region on an inlet side of the insertion member of the linear body extending through the insertion member by using a first angle acquiring unit;

a second angle acquiring step of acquiring a direction of the first portion of the linear body inserted into the body of the subject from an image of the linear body inserted into the body of the subject, and then, acquiring a rotational angle of the first portion of the linear body, by using a second angle acquiring unit; and a torque calculation step of calculating the torque based on a difference between the rotational angle of the second portion of the linear body acquired by the first angle acquiring unit and the rotational angle of the first portion of the linear body acquired by the second angle acquiring unit by using a torque calculation unit.

According to the 8th aspect, a magnitude of the torque applied to the flexible linear body can be acquired. In addition, even when the flexible linear body is made of a plurality of materials, the magnitude of the torque applied to the linear body can be acquired.

<First Embodiment>

FIG. 1 is a view showing a configuration on of a torque measurement apparatus 1 according to a first embodiment of the present invention. To measure a torque of a first liner body 10, the torque measurement apparatus 1 has a transparent image acquiring device 20, an imaging unit 31, a first torque acquiring unit 40, and an insertion length acquiring unit 60.

The first linear body 10 is a linear body which is a flexible and is an elongated member of circular cross section and has a curved portion 1020 (see FIG. 9) at a distal end thereof. Specifically, the first linear body 10 is a catheter or a guide wire. The first linear body 10 is inserted into a living body tube, such as a blood vessel, in a subject 80 through an insertion opening 90a of a sheath 90 (an example of an insertion member having an insertion opening through which the first linear body 10 is inserted into a body of the subject 80). The sheath 90 regulates movement of the first linear body 10 other than movement thereof only in an axial direction and rotational movement thereof about the axial direction. That is, the sheath 90 regulates movement of the linear body 10 in a radius direction orthogonal to the axial direction.

Figure 2:
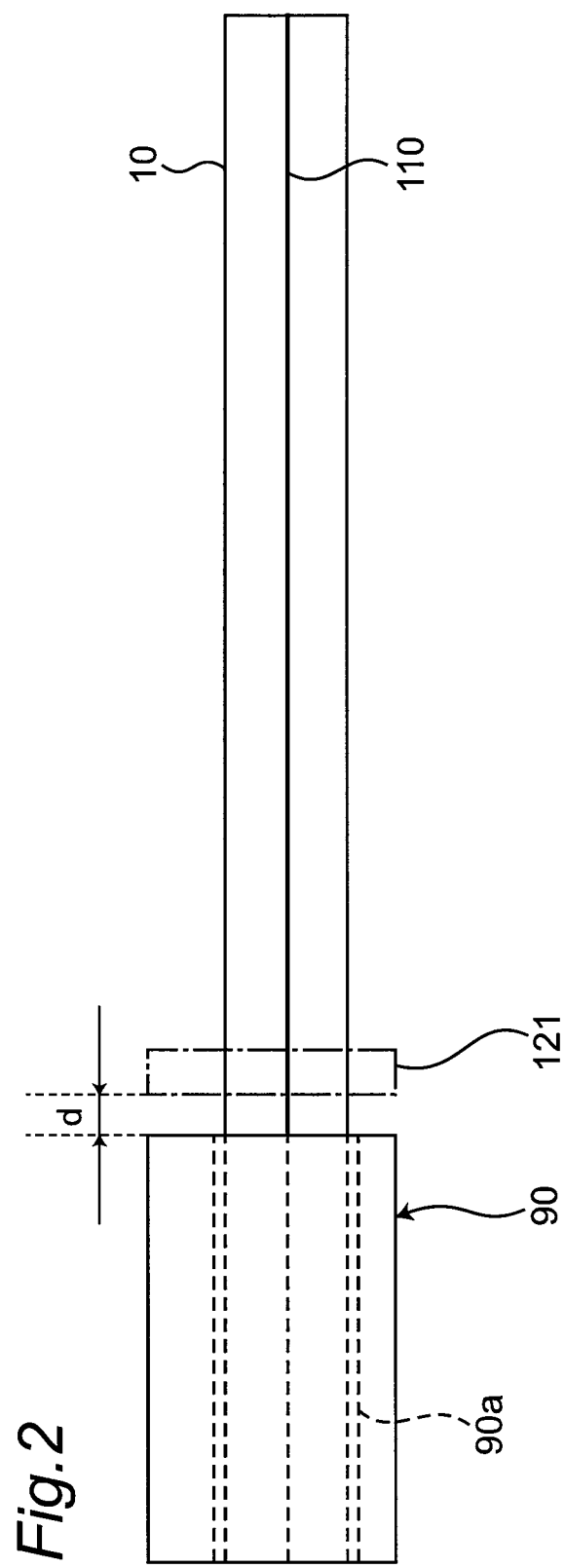
FIG. 2 is a view showing an example of a configuration of a first linear body according to the first embodiment.

FIG. 2 is an enlarged view of the first linear body 10 seen from top down in FIG. 1. On a surface of the first linear body 10, a linear characteristic portion parallel to the first linear body 10 in the axial direction (longitudinal direction), e.g., a line 110, is previously provided. The line 110 may be a line printed on an outer surface of the first linear body 10 or a line, such as a groove or a projection, with a height difference, formed in the outer surface of the first linear body 10. The line 110 may be a line made of gathered points. FIG. 2 shows only the first linear body 10 in a portion outside the body of the subject 80. Likewise, the line 110 is provided in a portion inside the body of the subject 80.

The transparent image acquiring device 20 has first and second X-ray generation units 23 and 24, and first and second X-ray detection units 21 and 22 corresponding to the respective X-ray generation units. The first and second X-ray generation units 23 and 24 irradiate a portion to be imaged of the patient (an example of the subject) 80 on a bed 70 with radioactive rays (e.g., X-rays). The first and second X-ray detection units 21 and 22 detect X-ray images transmitted through the patient 80.

The first and second X-ray generation units 23 and 24 each have an X-ray tube which generates an X-ray by using a high voltage, and an X-ray focusing device which controls an irradiation field by shielding a part of the X-ray. The first and second X-ray generation units 23 and 24 irradiate the patient 80 on the bed 70 with the X-rays so that the X-rays cross at different angles. The first and second X-ray detection units 21 and 22 receive the X-rays transmitted through the patient 80 from the first and second X-ray generation units 23 and 24, and then record image information. The first and second X-ray detection units 21 and 22 then output the recorded image information to the first torque acquiring unit 40. For instance, the first and second X-ray detection units 21 and 22 are each an FPD (Flat Panel Detector) which arranges an X-ray sensing layer therein and converts the X-ray into digital data for output. At the time of emitting the X-rays, the first and second X-ray detection units 21 and 22 output the image information showing the emitted X-ray images to the first torque acquiring unit 40.

The imaging unit 31 is a device (e.g., camera) which is fixed near the sheath 90 and images a position near an outside of an inlet side of the insertion opening 90a of the sheath 90 (in FIGS. 1 and 2) of the first linear body 10 constrained in the sheath 90 when the first linear body 10 is inserted and removed into and from the insertion opening 90a of the sheath 90. An imaging range of the imaging unit 31 is a predetermined region 121 in e.g., rectangular shape, in FIG. 2. A distance d from the sheath 90 to the predetermined region 121 is desirably short. For instance, in this context, d=0 mm.

Specifically, the imaging unit 31 is a line sensor including e.g., a CCD camera, and obtains brightness in each position in the predetermined region 121. Here, to simplify the description, the imaging unit 31 is arranged so that the predetermined region (rectangular imaging range) 121 is previously orthogonal to a center axis of the sheath 90 in the longitudinal direction. In addition, the imaging unit 31 is arranged so that a center of the predetermined region 121 comes to a position on an extension line of the center axis of the sheath 90.

The insertion length acquiring unit 60 acquires a length of the first linear body 10 inserted into the insertion opening 90a of the sheath 90. For instance, the insertion length acquiring unit 60 has a roller 61 which is contacted onto the surface of the first linear body 10, e.g., the catheter, and is rotated with advancement and retraction of the first linear body 10, an encoder 62 which measures a rotational angle of the roller 61, and a calculation unit 63 which calculates the insertion length from an amount of change in a rotational angle value of the encoder 62. The calculation unit 63 outputs a calculated insertion length to the first torque acquiring unit 40. The insertion length acquiring unit 60 may detect insertion length acquiring characteristic points provided on the surface of the first linear body 10 at predetermined length intervals to calculate an insertion length based on the number of detected passed insertion length acquiring characteristic points.

Figure 3:
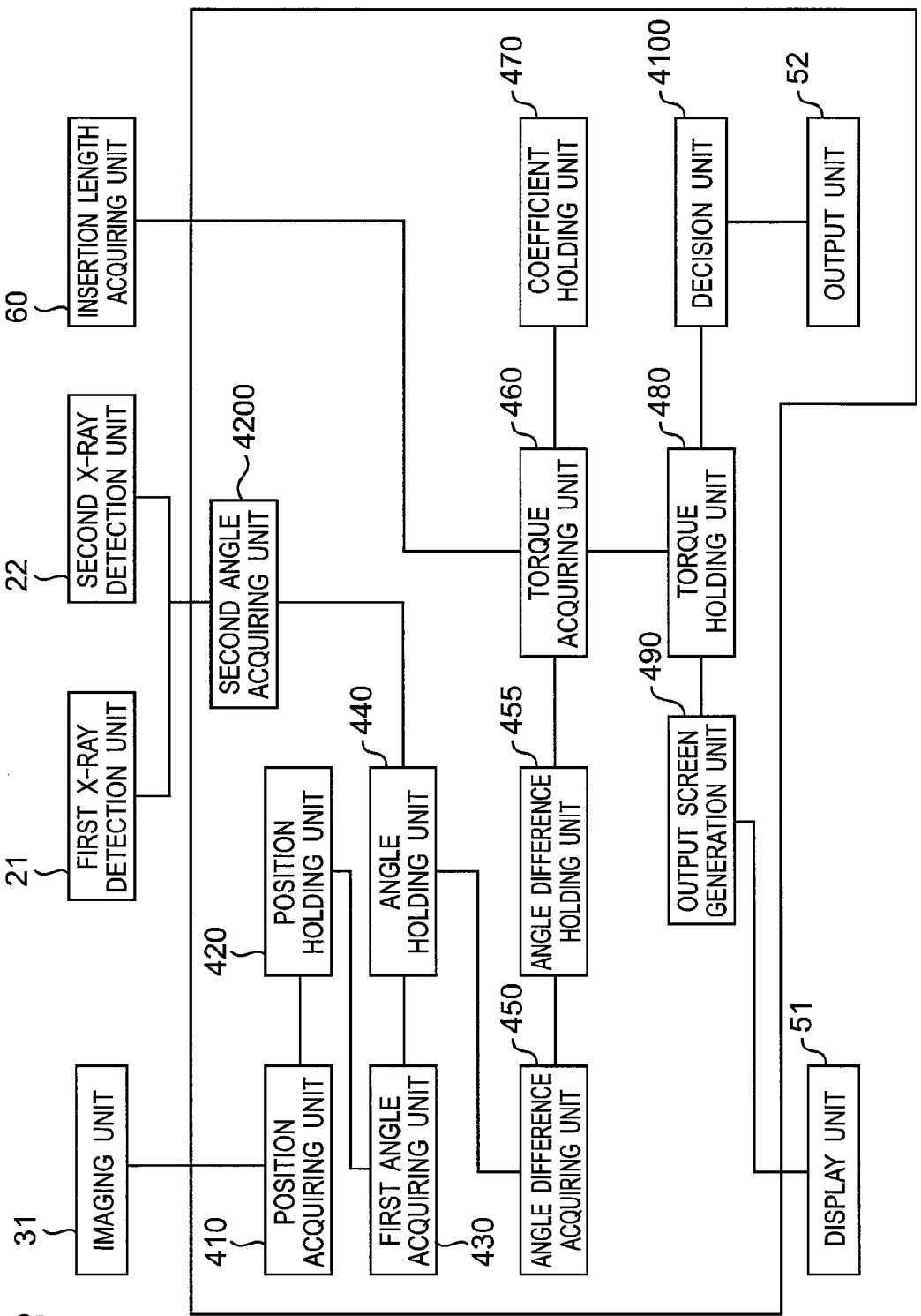
FIG. 3 is a view showing a configuration of a first torque acquiring unit according to the first embodiment.

The first torque acquiring unit 40 acquires a magnitude of a torque applied to the first linear body 10 based on the images acquired by the transparent image acquiring device (transparent image acquiring unit) 20 and the imaging unit 31 and the insertion length acquired by the insertion length acquiring unit 60. Specifically, the first torque acquiring unit 40 is realized by e.g., a computer. FIG. 3 is a view showing a configuration of the first torque acquiring unit 40. Each unit configuring the first torque acquiring unit 40 will be described below.

The first torque acquiring unit 40 has a position acquiring unit 410, a position holding unit 420, a first angle acquiring unit 430, a second angle acquiring unit 4200, an angle holding unit 440, an angle difference acquiring unit 450, an angle difference holding unit 455, a first torque calculation unit 460, a first coefficient holding unit 470, an output screen generation unit 490, a torque holding unit 480, a decision unit 4100, and an output unit 52.

The position holding unit 420 holds a position of the characteristic portion acquired by the later-described position acquiring unit 410, that is, the line 110, about the axial direction of the first linear body 10. Specifically, the position holding unit 420 is realized by a storage unit, such as a register in a computer device, cache, RAM, flexible disc, CD, DVD, SD card, magnetic card, or IC card (hereinafter, any unit named as a holding unit is realized by the same storage unit).

Figure 4:
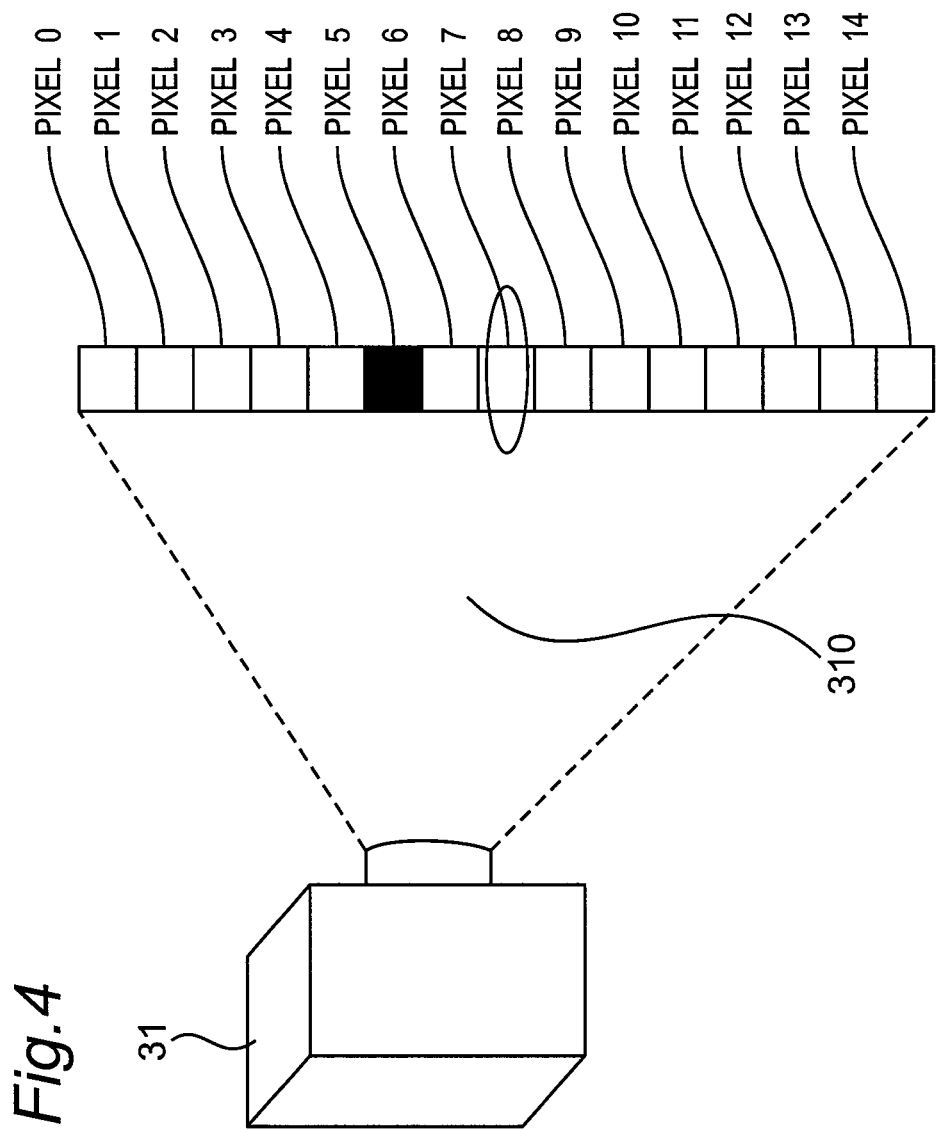
FIG. 4 is a view showing an example of the first linear body imaged by an imaging unit according to the first embodiment.

The image acquired by the imaging unit 31 is input to the position acquiring unit 410. From the image, the position acquiring unit 410 acquires, as the characteristic portion, the position of the line 110 in the predetermined region 121. For instance, the position acquiring unit 410 extracts a black position when the outer surface of the first linear body 10 itself is white and the line 110 is black. FIG. 4 is a view showing an image imaged by the imaging unit 31 which is a line sensor made of 15 pixels. Here, for simplification, the imaging unit 31 is arranged to image the entire width (perpendicular to the axial direction) of the first linear body 10 at the 15 pixels. As shown in FIG. 4, numbers (n=0, 1, 2, ..., 14) are assigned to the pixels from top (one end) to bottom (the other end) in that order. In FIG. 4, the position acquiring unit 410 performs a process for acquiring "5" which is a number of pixel 5.

Specifically, the position acquiring unit 410 decides whether brightness of each pixel in an image to be imaged is a threshold value or less, so that a number of the pixel having brightness which is the threshold value or less is the position of the line 110. When there are a plurality of pixels having brightness which is the threshold value or less, an average value of their numbers is the position of the line 110. Since pixel 5 is black and other pixels are white, the position acquiring unit 410 of the first embodiment acquires a value of the number of pixel 5 as the position of the line 110.

Figures 5, 6:
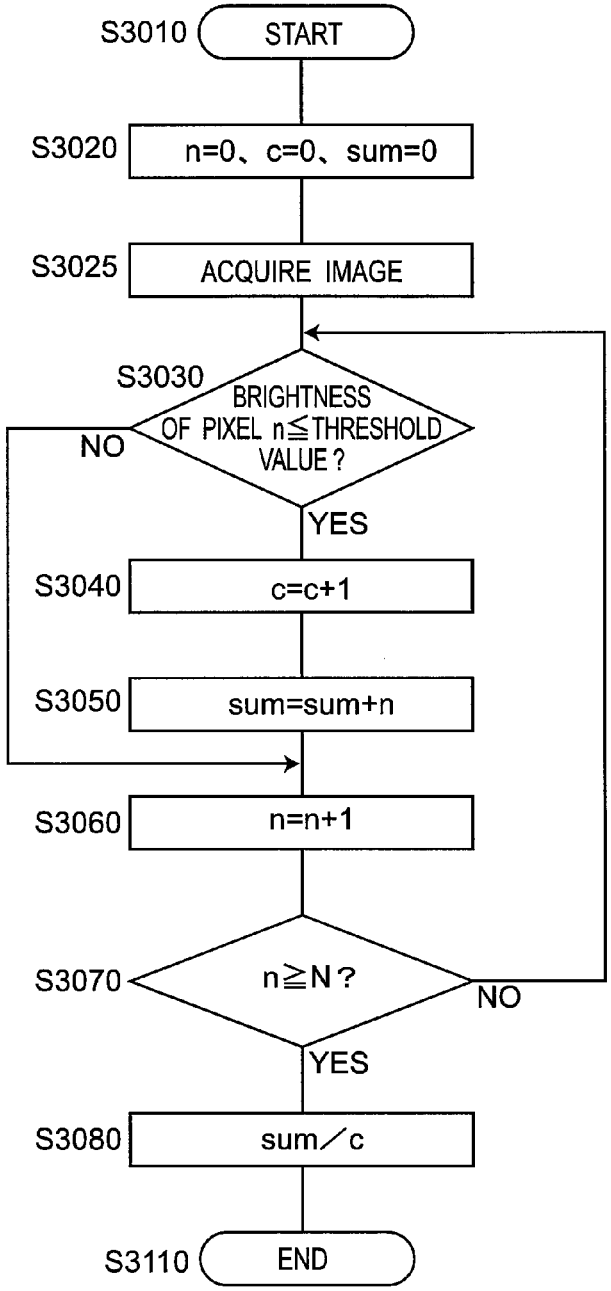
FIG. 5 is a flowchart showing a flow of a position acquiring process of a position acquiring unit according to the first embodiment.
FIG. 6 is a table-form view showing an example of a data structure of an angle holding unit according to the first embodiment.

FIG. 5 is a flowchart showing a flow of a position acquiring process of the position acquiring unit 410. The flow of the process of the position acquiring unit 410 will be described below.

Firstly, in step S3010, the position acquiring unit 410 starts the position acquiring process.

Next, in step S3020, the position acquiring unit 410 substitutes 0 into variable n, substitutes 0 into variable c, and substitutes 0 into variable sum. Here, the variable n is a variable which selects one of pixels 0 to 14 to be processed. The variable c is a variable which counts the number of pixels having brightness which is the threshold value or less. The variable sum is a variable which stores the total of the numbers of the pixels having brightness which is the threshold value or less. The variable is realized by a rewritable storage unit, such as a register in a computer device, cache, RAM, flexible disc, optical disc, or magnetic disc.

Next, in step S3025, the position acquiring unit 410 acquires an image imaged by the imaging unit 31.

Next, in step S3030, for the acquired image, the position acquiring unit 410 decides whether brightness of pixel n=0 is the predetermined threshold value or less. For instance, supposing that the brightness of the pixel takes the values of 0 to 255, the brightness of 0 is the darkest, and the brightness of 255 is the brightest, the threshold value is 50. As a decision result, when the brightness of pixel n=0 is the threshold value or less, the process is branched to step S3040. When the brightness of pixel n=0 is not the threshold value or less, the process is branched to step S3060.

In step S3040, the position acquiring unit 410 adds 1 to the value of the variable c. This process increases the number of counted pixels having brightness which is the threshold value or less, by 1.

Next, in step S3050, the position acquiring unit 410 adds n to the value of the variable sum.

Next, in step S3060, the position acquiring unit 410 adds 1 to the value of the variable n. Then, the next pixel is subjected to this process.

Next, in step S3070, the position acquiring unit 410 compares the value of the variable n with the number of pixels N (here, N=15 since the line sensor made of the 15 pixels is assumed). When the value of the variable n is N or more, the process is branched to step S3080. When the value of the variable n is not N or more, the process is branched to step S3030. That is, the process from steps S3030 to S3060 is repeatedly executed to all the pixels. After all the pixels in the image data in the imaging unit 31 are processed, the process is branched to step S3080.

In step S3080, the position acquiring unit 410 calculates sum/c. This process is a process for calculating an average of the numbers of the pixels having brightness which is the threshold value or less by the position acquiring unit 410. The calculated average value is stored, as the position of the line 110, into the position holding unit 420.

In step S3110, the position acquiring unit 410 ends a series of processes for the image data of the imaging unit 31.

The position holding unit 420 holds the position of the characteristic portion acquired by the position acquiring unit 410, that is, the line 110, for each image data of the imaging unit 31. Specifically, the holding operation of the position of the line 110 is realized by a storage unit or means, such as a register in a computer device, cache, RAM, flexible disc, CD, DVD, SD card, magnetic card, or IC card (hereinafter, any unit or means named as a holding unit is realized by the same storage unit or means).

The first angle acquiring unit 430 uses the position of the line 110 in the predetermined region 121 acquired by the position acquiring unit 410 to calculate a rotational angle of the first linear body 10 about the axial direction in the predetermined region 121.

The angle holding unit 440 holds rotational angles $\theta_1$ and $\alpha$ of the characteristic portion and the rotational angle acquiring characteristic point acquired by the later-described first angle acquiring unit 430 and second angle acquiring unit 4200. FIG. 6 is a table-form view showing an example of a data structure of the angle holding unit 440. The angle holding unit 440 has an array which holds two angles, so that elements in the array can be discriminated by identifiers. That is, the angle holding unit 420 holds angle information of identifier 0 acquired by the first angle acquiring unit 430, and angle information of the identifier 1 acquired by the second angle acquiring unit 4200. FIG. 6 shows that these pieces of information are "0.28975 (radian)" (approximately 17°) and "−0.4429 (radian)" (approximately −25°), respectively. The data of the rotational angles of the line 110 held by the angle holding unit 440 are input to the angle difference acquiring unit 450.

Figure 7:
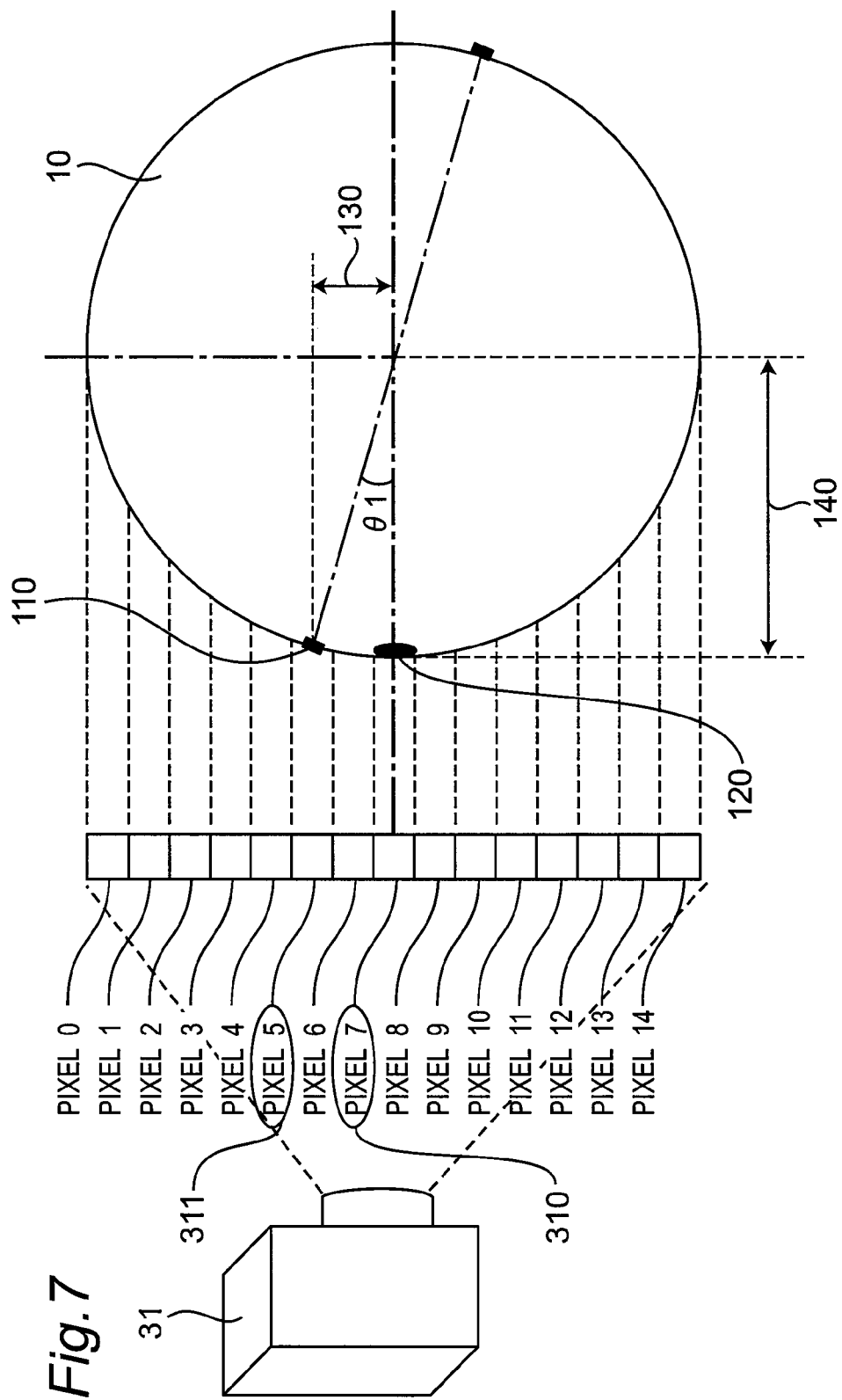
FIG. 7 is a cross-sectional view of the first linear body according to the first embodiment.

Here, a relation between the position of the line 110 and the rotational angle of the linear body will be described with reference to a cross-sectional view of the first linear body 10 in FIG. 7. A circle at the right end of FIG. 7 is a cross-sectional shape (circle) of the first linear body 10. The imaging unit 31 is shown at the left end of FIG. 7. The imaging unit 31 has elements imaging pixels 0 to 14, which are enlarged in square shape in the middle of FIG. 7. In addition, between the cross-sectional shape (circle) of the first linear body 10 and pixels 0 to 14 in FIG. 7, boundaries between ranges imaged by the pixels on an outer circumferential surface of the first linear body 10 are indicated by dotted lines.

Pixels 0 to 14 of the line sensor as the imaging unit 31 are arranged to correspond to ends T1 and T2 of the first linear body 10 in a diameter direction (t direction). Among these, pixel 7 is a pixel with respect to the center position in the imaged range (predetermined region) (here, pixels 0 to 14) 121 of the first linear body 10 in the image imaged by the imaging unit 31. Hereinafter, pixel 7 is referred to as a center pixel 310. A surface portion of the first linear body 10 imaged at the center pixel 310 is a center position 120. A radius 140 is a length of a radius of the first linear body 10 in the image imaged by the imaging unit 31. In FIG. 7, the length of the radius is a length from the center pixel 310 (pixel 7) to pixel 0 or 14 which images the end T1 or T2 of the first linear body 10, and is seven pixels from 14−7=7.

In FIG. 7, since pixel 5 is black and other pixels are white, the value of the number of pixel 5 is acquired as the position of the line 110 by the position acquiring unit 410. That is, pixel 5 is the position of the line 110 acquired by the position acquiring unit 410. Hereinafter, pixel 5 is referred to as a line position pixel 311. A distance 130 is a distance from the line position pixel 311 to the center pixel 310 on the image. Here, 7−5=2.

The angle $\theta_1$ represents a rotational angle of the line 110 from the center position 120. From a trigonometric function definition, the angle $\theta_1$ is:

$$\sin \theta_1 = (\text{distance } 130)/(\text{radius } 140) \qquad \text{(Equation 1)}.$$

From Equation 1, $$\theta_1 = \arcsin\{(\text{distance } 130)/(\text{radius } 140)\} \quad \text{(Equation 2)}$$

Here, function arcsin is an inverse function of the sin function. In FIG. 7, $\theta_1 = \arcsin(2/7)$.

Figure 8:
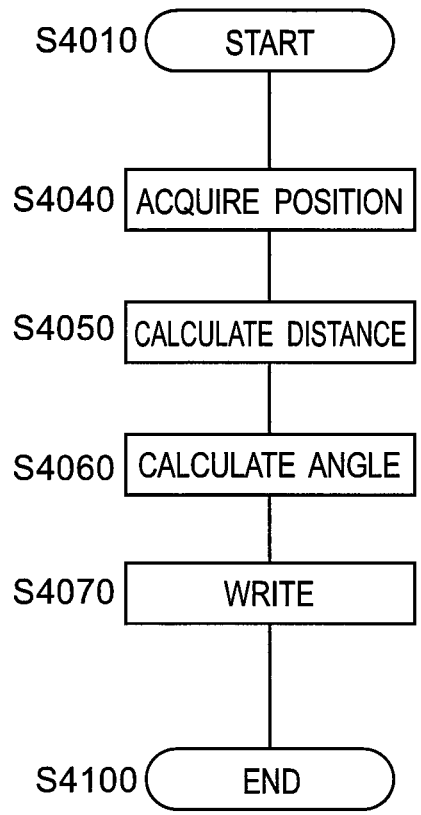
FIG. 8 is a flowchart showing a flow of a process of a first angle acquiring unit according to the first embodiment.

In this way, the first angle acquiring unit 430 performs the process for calculating the angle $\theta_1$ based on the data of the position of the line 110 held by the position holding unit 420 and the radius information held by the storage means or unit of the first angle acquiring unit 430. Here, for simplification, the radius 140 (the value is 7) is previously held by the storage means or unit of the first angle acquiring unit 430. Hereinafter, an angle acquiring process of the first angle acquiring unit 430 will be described with reference to the flowchart in FIG. 8. Here, the storage means or unit holds the value "7" of the radius 140.

Firstly, in step S4010, the first angle acquiring unit 430 starts the angle acquiring process.

Next, in step S4040, the first angle acquiring unit 430 acquires a position of the line position pixel 311 (data of a position of the line 110) as position information from the position holding unit 420.

Next, in step S4050, the first angle acquiring unit 430 calculates a distance from the center pixel 310 to the line position pixel 311. That is, the first angle acquiring unit 430 calculates a value acquired by subtracting the value of the position acquired in step S4040 from the pixel number (here, always 7) of the center pixel 310. Here, the pixel number (7) of the center pixel 310 is previously held in the storage means or unit incorporated into the first angle acquiring unit 430 (in addition to the above storage means, the storage means or unit here may be a nonvolatile memory, such as a ROM or CD-ROM). In FIG. 7, 7−5=2.

Next, in step S4060, the first angle acquiring unit 430 calculates a rotational angle $\theta_1$ based on Equation 2. In FIG. 7, $\theta_1 = \arcsin(2/7)$, that is, "2.8975".

Next, in step S4070, the first angle acquiring unit 430 stores the value of the rotational angle $\theta_1$ calculated in the previous step into the angle holding unit 440. Here, the data is stored into the field of the identifier 0 of the angle holding unit 420.

Next, in step S4100, the first angle acquiring unit 430 ends the process.

From the transparent image acquired by imaging the inside of the body of the subject 80 by the transparent image acquiring device 20, the second angle acquiring unit 4200 acquires a direction of a curved shape of the distal end of the first linear body 10 in the body of the subject 80, and then acquires a rotational angle $\alpha$ of the distal end of the first linear body 10. Here, for simplifying the description, a method for acquiring the direction of the first linear body 10 which is previously provided with rotational angle acquiring characteristic points 151 to 153 will be described.

Figure 9:
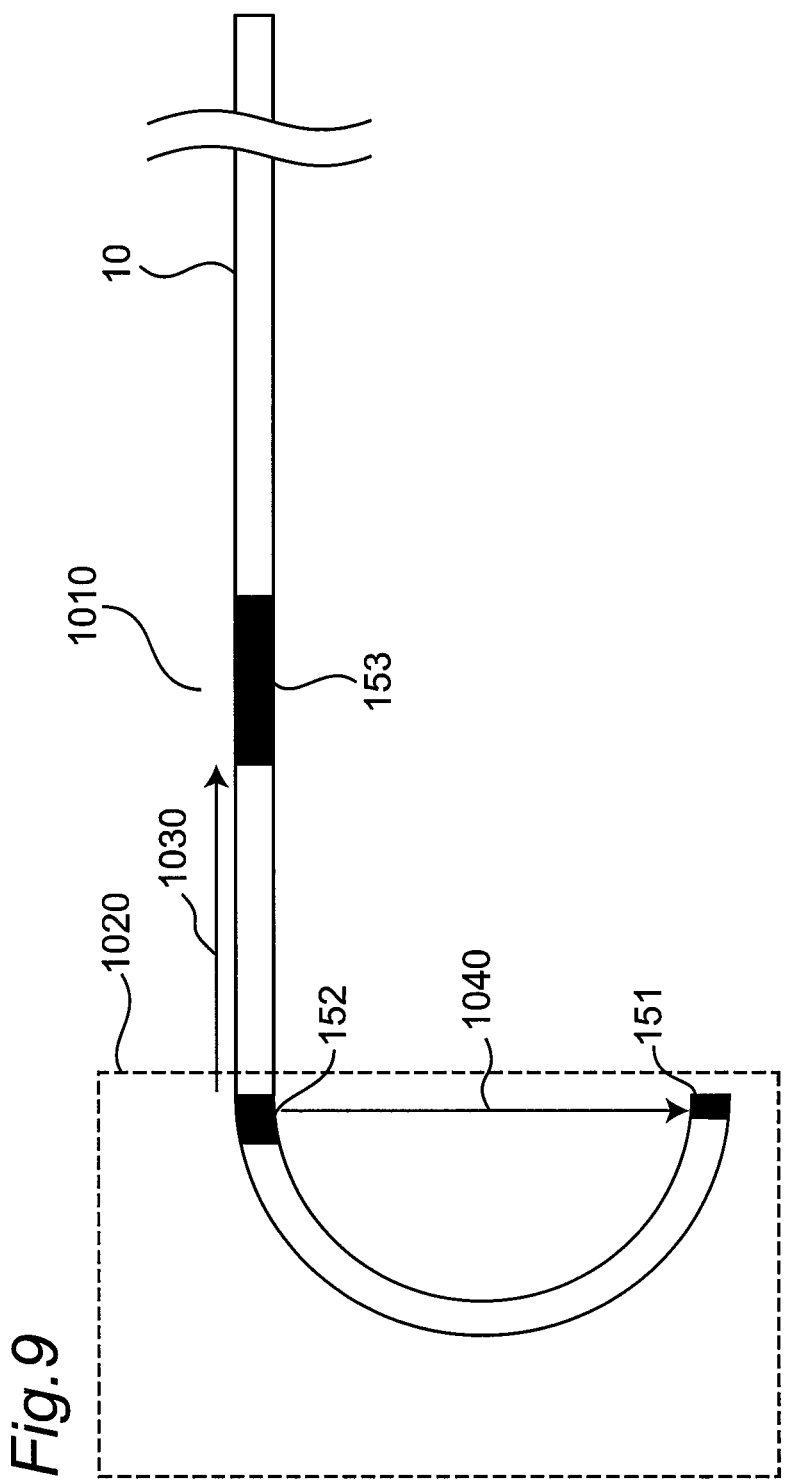
FIG. 9 is a view showing an example of a configuration of the first linear body according to the first embodiment.

FIG. 9 is a view showing the distal end portion of the first linear body 10. The first linear body 10 has a straight marker 1010, and the curved portion 1020 curved from an end of the marker 1010. The first characteristic point 151 is provided at an end of the curved port ion 1020 and in the entire circumference of the first linear body 10 in a circumferential direction thereof, and is made of a material including gold. The second characteristic point 152 is provided in a boundary portion between the curved portion 1020 and the marker 1010 and in the entire circumference of the first linear body 10 in the circumferential direction. The third characteristic point 153 is provided in a predetermined position apart from the second characteristic point 152 (by e.g., 10 mm) and in a position in the entire circumference of the marker 1010 in the circumferential direction. The material of the second and third characteristic points 152 and 153 is the same as the first characteristic point 151. Widths of the first, second, third characteristic points 151, 152, and 153 are 1 mm, 3 mm, and 9 mm, respectively.

The portions of the first to third characteristic points 151 to 153 of the first linear body 10 include gold. The first to third characteristic points 151 to 153 through which the X-ray transmits are observed at brightness lower than peripheral portions thereof.

As shown in FIG. 12, a vector 1030 is a vector connecting the second characteristic point 152 and the third characteristic point 153. A vector 1040 is a vector connecting the second characteristic point 152 and the first characteristic point 151.

At this time, from an outer product definition, a direction of an outer product of the vectors 1030 and 1040 is a direction from a back side of the sheet to a front side thereof.

Figure 10:
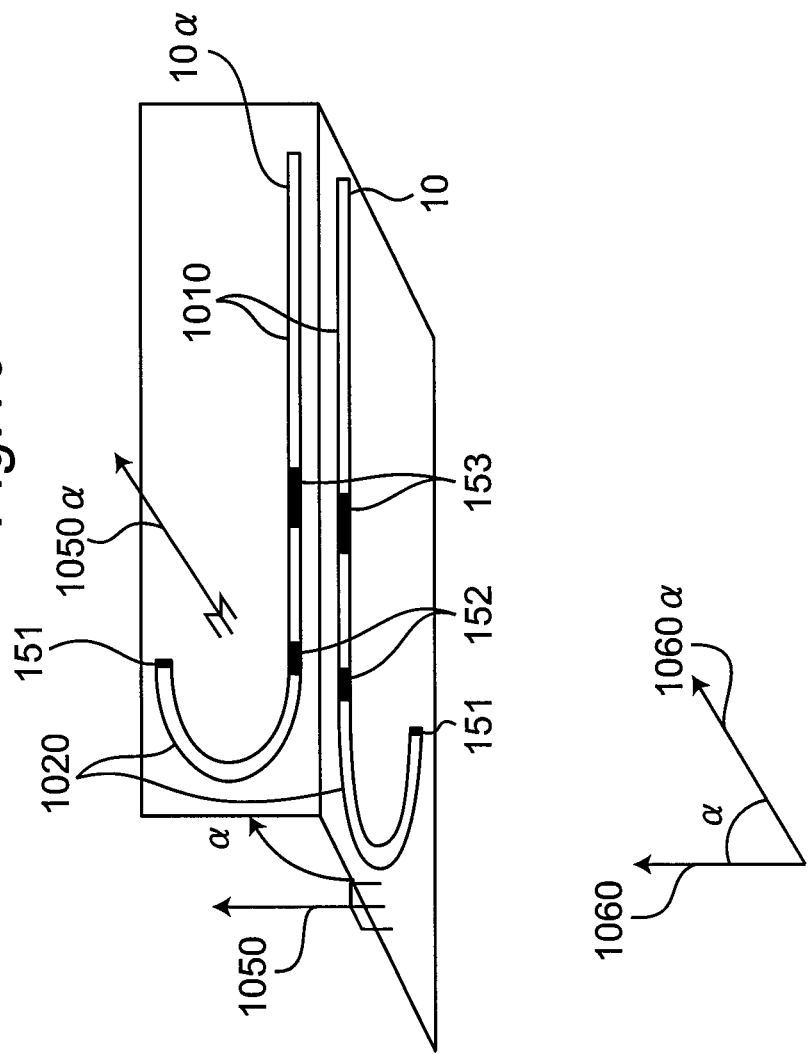
FIG. 10 is a view showing rotation of a curved portion according to the first embodiment.

FIG. 10 is a view showing a state of rotation of the curved portion 1020 by rotation of the first linear body 10.

In FIG. 10, the lower one of the illustrated two first linear bodies 10 shows a position of the first linear body 10 before rotation. A first linear body 10$\alpha$ on the upper side shows a position of the first linear body 10 after rotation. A vector 1050 shows an outer product before rotation. The first linear body 10$\alpha$ shows a position of the first linear body 10 rotated by the angle $\alpha$. A vector 1050$\alpha$ shows an outer product after rotation.

In FIG. 10, a vector 1060 is a vector shown by moving a base point to a different position without changing a direction of the vector 1050.

A vector 1060$\alpha$ is a vector shown by moving a base point to a different position without changing a direction of the vector 1050$\alpha$ so as to have the same base point as the vector 1060. At this time, an angle formed between the vectors 1060 and 1060$\alpha$ is equal to the angle $\alpha$.

The second rotational angle acquiring unit 4200 acquires the angle $\alpha$ formed between the vectors 1050 and 1050$\alpha$ (this is equal to the angle $\alpha$ formed between the vectors 1060 and 1060$\alpha$), and then acquires the rotational angle $\alpha$ of the curved portion 1020.

Figure 11:
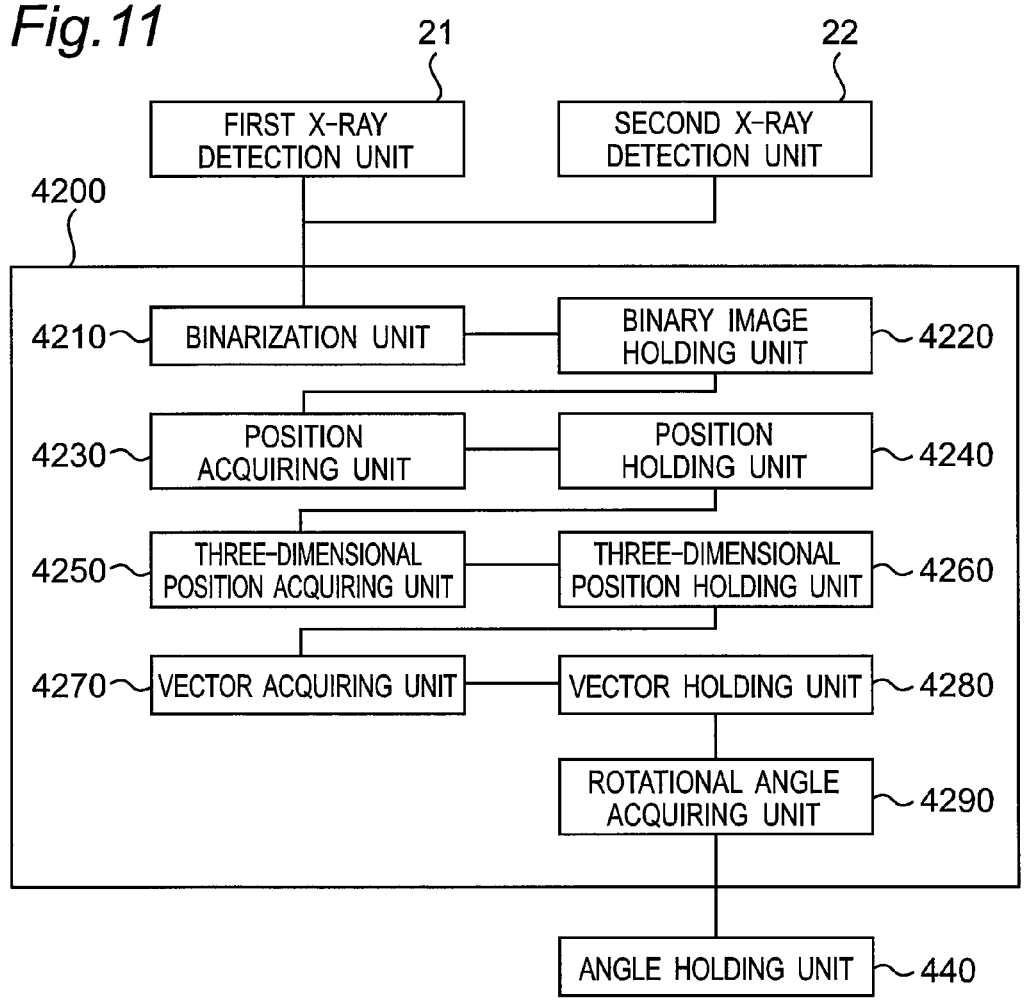
FIG. 11 is a view showing a configuration of a second angle acquiring unit according to the first embodiment.

Each unit configuring the second rotational angle acquiring unit 4200 will be described below. FIG. 11 is a view showing a configuration of the second angle acquiring unit 4200. The second angle acquiring unit 4200 has a binarization unit 4210, a binary image holding unit 4220, a position acquiring unit 4230, a position holding unit 4240, a three-dimensional position acquiring unit 4250, a three-dimensional position holding unit 4260, a vector acquiring unit 4270, a vector holding unit 4280, and a rotational angle acquiring unit 4290.

The binarization unit 4210 binarizes the X-ray images acquired by the first and second X-ray detection units 21 and 22, and extracts the ranges of the first to third characteristic points 151 to 153. The binarization unit 4210 outputs the extraction result information, that is, the images binarized by the binarization unit 4210, to the binary image holding unit 4220. For instance, when the image obtained by the first X-ray detection unit 21 is the image shown in FIG. 12, the image obtained by binarization is shown in FIG. 13. In FIG. 13, the first to third characteristic points 151 to remain.

The binary image holding unit 4220 holds the image binarized by the binarization unit 4210.

The position acquiring unit 4230 acquires positions of the first to third characteristic points 151 to 153 from a binary image held by the binary image holding unit 4220. In the binary image held by the binary image holding unit 4220, the largest region is the third characteristic point 153, the second largest region is the second characteristic point 152, and the third largest region is the region of the first characteristic point 151. A center position in each region is stored in the position holding unit 4240. The position acquiring unit 4230 performs the position acquiring process to both binary images acquired from the first and second X-ray detection units 21 and 22.

The position holding unit 4240 stores center positions of the first to third characteristic points 151 to 153 on the image acquired by the position acquiring unit 4230. FIG. 14 shows an example of a data structure of the position holding unit 4240.

In FIG. 14, the image number "0" represents image information of the first X-ray detection unit 21, and the image number "1" represents image information of the second X-ray detection unit 22. The characteristic point "0" corresponds to the first characteristic point 151, the characteristic point "1" corresponds to the second characteristic point 152, and the characteristic point "2" corresponds to the third characteristic point 153. The first row of the data structure of the position holding unit 4240 is a row which stores the position of the first characteristic point 151 in the binary image of the first X-ray detection unit 21. The first column of the data structure of the position holding unit 4240 stores a value showing the order of the pixel away from an origin o in FIG. 12 in an x-axis direction where the first characteristic point 151 is present. The second column of the data structure of the position holding unit 4240 stores a value showing the order of the pixel away from the origin o in FIG. 12 in a y-axis direction where the first characteristic point 151 is present. Likewise, the second and third rows of the data structure of the position holding unit 4240 are rows which store the positions of the second and third characteristic points 152 and 153 in the binary image of the first X-ray detection unit 21. In addition, the fourth, fifth, and sixth rows of the data structure of the position holding unit 4240 are rows which store the positions of the first to third characteristic points 151, 152, and 153 in the binary image of the second X-ray detection unit 22. For each row of the data structure, there are a column which stores an x coordinate and a column which stores a y coordinate.

Figures 15, 16, 17:
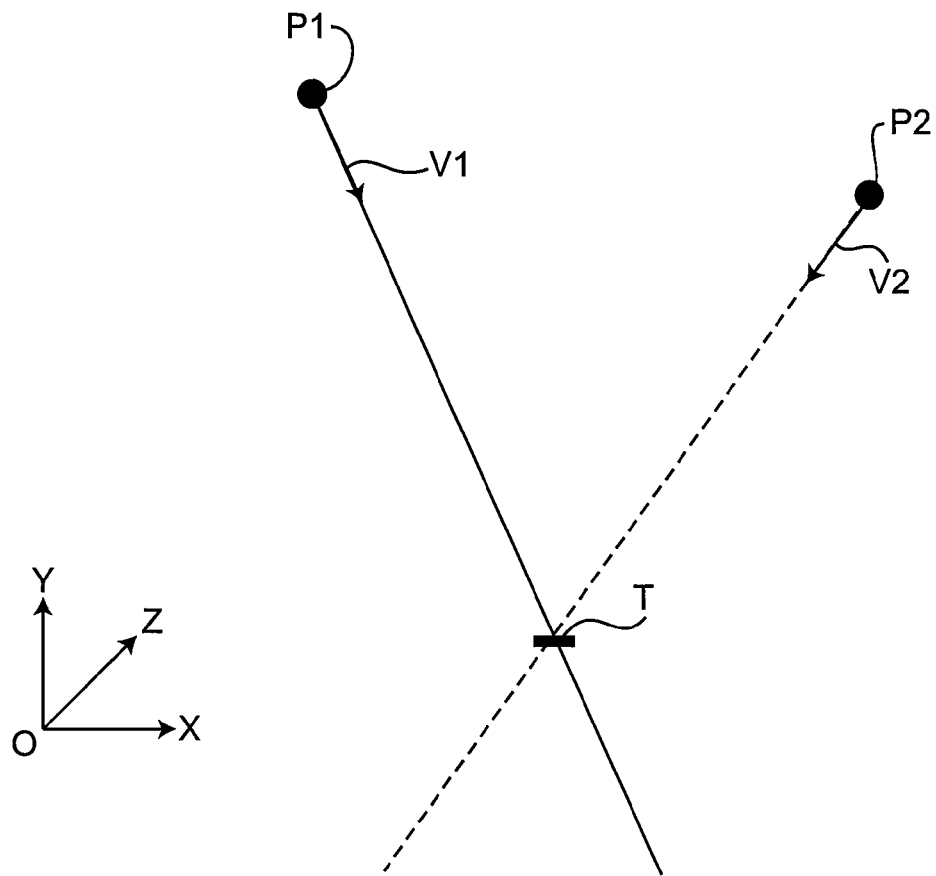
FIG. 15 is a view showing three-dimensional position acquiring by triangulation according to the first embodiment.
FIG. 16 is a table-form view showing an example of a data structure of a three-dimensional position holding unit according to the first embodiment.
FIG. 17 is a table-form view showing an example of a data structure of a vector holding unit according to the first embodiment.

Three-dimensional position acquiring unit 4250 calculates three-dimensional positions of the first to third characteristic points 151 to 153 based on data held by the position holding unit 4240. In a stereo image process, a distance from two cameras placed in different positions to a target (here, the characteristic point) T is measured by using the principle of triangulation, thereby acquiring a position of the target (here, the characteristic point) T. FIG. 15 is a view showing three-dimensional position acquiring by triangulation according to the first embodiment. In FIG. 15, T shows the target to be observed. O is an origin of the three-dimensional XYZ coordinates. Supposing that in position P1, the target to be observed T is observed in a direction of a vector V1. At this point, the target T is present in any of positions in a solid line. That is, a vector OT from the origin O to the target T is expressed by Equation 3. Here, s is an unknown number.

$$\overrightarrow{OT} = \overrightarrow{P1} + s\overrightarrow{V1} \quad \text{(Equation 3)}$$

Likewise, supposing that in position P2, the target to be observed T is observed in a direction of a vector V2. At this point, the target T is present in any of positions in a dotted line. That is, the vector OT from the origin O to the target T is expressed by Equation 4. Here, $t_a$ is an unknown number.

$$\overrightarrow{OT} = \overrightarrow{P2} + t_a\overrightarrow{V2} \quad \text{(Equation 4)}$$

From Equations 3 and 4, $$\overrightarrow{P1} + s\overrightarrow{V1} = \overrightarrow{P2} + t_a\overrightarrow{V2} \quad \text{(Equation 5)}$$

When each vector in Equation 5 is known, two unknown numbers are s and $t_a$. Since each vector is three-dimensional, a cubic equation with two unknowns is solved to calculate s and $t_a$. From the calculated s and $t_a$, the vector OT, that is, $\overrightarrow{OT}$ is calculated.

The three-dimensional position acquiring unit 4250 acquires, from the position information holding unit 4240, a position of the first characteristic point 151 from the two cameras, and then acquires the position of the first characteristic point 151 by the stereo image process. Likewise, the positions of the second and third characteristic points 152 and 153 are acquired by the three-dimensional position acquiring unit 4250. The three-dimensional position acquiring unit 4250 holds the acquired three-dimensional positions of the first to third characteristic points 151 to 153 in the three-dimensional position holding unit 4260.

The three-dimensional position holding unit 4260 holds three-dimensional positions of the first to third characteristic points 151 to 153 acquired from the three-dimensional position acquiring unit 4250. FIG. 16 shows an example of a data structure held by the three-dimensional position holding unit 4260.

In FIG. 16, the characteristic point "0" corresponds to the first characteristic point 151, the characteristic point "1" corresponds to the second characteristic point 152, and the characteristic point "2" corresponds to the third characteristic point 153. "X", "Y", and "Z" represent the X coordinate, Y coordinate, and Z coordinate of the first to third characteristic points 151 to 153. For the three-dimensional positions of the XYZ coordinates, the positions from the origin O in the X-axis, Y-axis, and Z-axis directions in FIG. 1 are used. Its unit is mm (millimeter).

The first row of the data structure of the three-dimensional position holding unit 4260 is a row which stores the three-dimensional position of the first characteristic point 151. Likewise, the second and third rows of the data structure are rows which store the three-dimensional positions of the second and third characteristic points 152 and 153. Each row of the data structure includes a column which stores the X coordinate of the characteristic point, a column which stores the Y coordinate thereof, and a column which stores the Z coordinate thereof.

The vector acquiring unit 4270 acquires the vectors 1030 and 1040 in FIG. 12 based on three-dimensional positions of the first to third characteristic points 151 to 153 held by the three-dimensional position holding unit 4260. The vector 1030 is a vector from the second characteristic point 152 to the third characteristic point 153. When the second characteristic point 152 is ($x_2$, $y_2$, $z_2$) and the third characteristic point 153 is ($x_3$, $y_3$, $z_3$), the vector 1030 is ($x_3-x_2$, $y_3-y_2$, $z_3-z_2$). The vector acquiring unit 4270 acquires coordinates of the first to third characteristic points 151 to 153 from the position holding unit 4240 to perform the calculation of the vector 1030. In addition, the vector 1040 is a vector from the second characteristic point 152 to the first characteristic point 151. When the second characteristic point 152 is ($x_2$, $y_2$, $z_2$) and the first characteristic point 151 is ($x_1$, $y_1$, $z_1$), the vector 1040 is ($x_1-x_2$, $y_1-y_2$, $z_1-z_2$). The vector acquiring unit 4270 acquires the coordinates of the first to third characteristic points 151 to 153 from the position holding unit 4240 to perform the calculation of the vector 1040.

The vector holding unit 4280 holds the vectors 1030 and 1040 acquired by the vector acquiring unit 4270. FIG. 17 is a table-form view showing an example of a data structure of the vector holding unit 4280. The vector "0" corresponds to the vector 1030, and the vector "1" corresponds to the vector 1040. "X", "Y", and "Z" represent components of the vectors 1030 and 1040 in the X, Y, and Z coordinate directions. Each component is a component from the origin O in the X-axis, Y-axis, and Z-axis directions in FIG. 1. Its unit is mm (millimeter).

The first row of the data structure of the vector holding unit 4280 holds the vector 1030, and the second row of the data structure thereof holds the vector 1040. Each row of the data structure includes a column holding the X coordinate, a column holding the Y coordinate, and a column holding the Z coordinate.

Figures 18, 19:
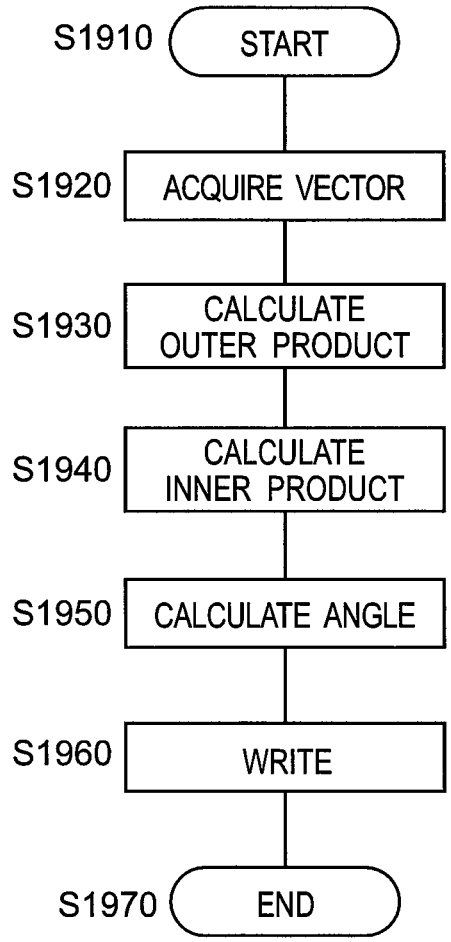
FIG. 18 is a flowchart showing a flow of a process of a rotational angle acquiring unit according to the first embodiment.
FIG. 19 is a table-form view showing a screen generated by an output screen generation unit according to the first embodiment.

The rotational angle acquiring unit 4290 acquires a rotational angle of the curved portion 1020 of the first linear body 10 from the vectors held by the vector holding unit 4280. FIG. 18 is a flowchart showing a flow of a rotational angle acquiring process of the rotational angle acquiring unit 4290.

Firstly, in step S1910, the rotational angle acquiring unit 4290 starts the rotational angle acquiring process.

Next, in step S1920, the rotational angle acquiring unit 4290 acquires the vectors 1030 and 1040 from the vector holding unit 4280. Here, the vector 1030 is $(vx_1, vy_1, vz_1)$ and the vector 1040 is $(vx_2, vy_2, vz_2)$.

Next, in step S1930, the rotational angle acquiring unit 4290 calculates an outer product vector V3 of the vectors 1030 and 1040. Here, the rotational angle acquiring unit 4290 calculates:

$$(vx_3, vy_3, vz_3) = (Vx_1 \times vy_2 - vy_1 \times vx_2, vy_1 \times vz_2 - vz_1 \times vy_2, vz_1 \times vx_2 - vx_1 \times vz_2)$$ (Equation 6).

Next, in step S1940, the rotational angle acquiring unit 4290 calculates an inner product of the outer product vector V3 calculated in the previous step and an outer product vector V4 before rotation. Here, supposing that, for simplification, the outer product vector before rotation (the vector 1050 in FIG. 10) is previously held in the memory device. Here, the outer product vector V4 before rotation is $(vx_4, vy_4, vz_4)$. At this time, the inner product is:

$$vx_3 \times vx_4 + vy_3 \times vy_4 + vz_3 \times vz_4$$ (Equation 7).

Next, in step S1950, the rotational angle acquiring unit 4290 calculates an angle α by using an inner product formula. When the inner product of vectors V3 and V4 is <V3, V4> and norms of the vectors are |V3| and |V4|, the following formula is established:

$$\cos \alpha = <V3, V4>/(|V3| |V4|)$$ (Equation 8).

Therefore, $$\alpha = \arccos(<V3, V4>/(|V3| |V4|))$$ (Equation 9).

Here, arccos is an inverse function of the cosine. In addition, |V3| and |V4| are expressed by the following equations:

$$|V3| = \sqrt{vx_3^2 + vy_3^2 + vz_3^2}$$ (Equation 10); and $$|V4| = \sqrt{vx_4^2 + vy_4^2 + vz_4^2}$$ (Equation 11).

From the above, $$\alpha = \arccos\left(\frac{vx_3 vx_4 + vy_3 vy_4 + vz_3 vz_4}{\sqrt{vx_3^2 + vy_3^2 + vz_3^2} \sqrt{vx_4^2 + vy_4^2 + vz_4^2}}\right)$$ (Equation 12).

The rotational angle acquiring unit 4290 calculates a rotational angle α based on Equation 12.

Next, in step S1960, the rotational angle acquiring unit 4290 writes the acquired rotational angle into the field of the identifier 1 of the angle holding unit 440.

Next, in step S1970, the rotational angle acquiring unit 4290 ends the process.

The above is the description of the rotational angle acquiring unit 4290.

The angle difference acquiring unit 450 acquires a difference between two angles held by the angle holding unit 440. That is, the angle difference acquiring unit 450 acquires an angle of the identifier 0 and an angle of the identifier 1 from the angle holding unit 440, calculates the difference, and stores the difference into the angle difference holding unit 455.

An angle difference holding unit 455 holds the angle difference calculated by the angle difference acquiring unit 450.

The first coefficient holding unit 470 holds a coefficient showing twistability of the first linear body 10.

In general, when the angle difference between two points which are apart from each other by a distance L in the axial direction of the first linear body 10 is θ, a torque T applied to the first linear body 10 is:

$$T = G_1 \times Ip_1 \times \theta / L$$ (Equation 13).

Equation 13 shows that torque T applied to the first linear body 10 is proportional to an angle difference θ between the two points which are apart from each other by the predetermined distance L in the axial direction of the first linear body 10, and includes the coefficient showing twistability of the first linear body 10.

Here, $G_1$ as a coefficient is a transverse elasticity modulus, and is a value determined by the material of the first linear body 10. $Ip_1$ as a coefficient is a polar moment of inertia of area, and is a value determined by the shape of the first linear body 10. More specifically, the polar moment of inertia of area is a value determined by the length of the radius of the first linear body 10. L as a coefficient is a value of the distance between the two points in which the angle difference is measured.

The first coefficient holding unit 470 holds, in the above equation:

$$G_1 \times Ip_1$$ (Equation 14).

In the following description, the value of Equation 14 is $P_0$. At this time, Equation 13 is:

$$T = P_0 \times \theta / L$$ (Equation 13-2).

The first torque calculation unit 460 acquires the value of Equation 14 held by the first coefficient holding unit 470, an insertion length L acquired by the insertion length acquiring unit 60, and the angle difference θ held by the angle difference holding unit 455, calculates a torque based on Equation 13-2, and stores the torque into the torque holding unit 480.

The torque holding unit 480 holds the torque acquired by the first torque calculation unit 460.

The output screen generation unit 490 acquires the torque value from the torque holding unit 480, and then generates a screen displayed on a later-described display unit 51. FIG. 19 shows a screen generated by the output screen generation unit 490. On the screen, "torque" is displayed in the left section in a table with one row and two columns, and the torque value acquired from the torque holding unit 480 is displayed in the right section.

The decision unit 4100 decides whether or not the torque acquired by the first torque calculation unit 460 and held by the torque holding unit 480 is larger than a predetermined value. Specifically, the decision unit 4100 decides whether or not an absolute value of the torque value held by the torque holding unit 480 is larger than a predetermined threshold value. When deciding that the absolute value of the torque value is larger than the predetermined threshold value, the decision unit 4100 requests the later-described output unit 52 to output this information.

The output unit 52 performs outputting based on the torque value acquired by the first torque acquiring unit 40.

The display unit 51 functions as an example of a presentation unit, and displays the screen generated by the output screen generation unit 490. Specifically, the display unit 51 is a display.

The output unit 52 gives an alarm sound when there is the request from the decision unit 4100. Specifically, the output unit 52 is a speaker. When an alarm lamp is lit instead of the alarm sound, the output unit 52 may be an alarm lamp.

Here, the imaging unit 31 is a line sensor, but may be a CCD camera. In this case, firstly, an end of the sheath 90 is extracted in the imaging process. For instance, in FIG. 2, the end of the sheath 90 is made blue, so that the blue region is extracted from the image. Then, a region on the right side of the end extracted from the image (e.g., a collection of pixels in which each third pixel in the right direction from each pixel at the extracted end) is extracted. Further, in the extracted region, both ends of the line 110 are extracted, so that the range of from end to end of the line 110 is the range (predetermined region) 121.

In addition, the sheath 90 may be formed of a transparent member. In that case, the range (predetermined region) 121 is not always required to be the outside range of the sheath 90, and may be inside the sheath 90.

Here, for simplification, the first linear body 10 has one line 110, but may have a plurality of lines 110. By using such a configuration, a torque can be calculated even when the first linear body 10 is moved from the imaging unit 31 to a position in which the line 110 is not seen. For instance, lines 110, 111, 112, and 113 in colors 0, 1, 2, and 3 which are different at each 90° are provided on the surface of the first linear body 10. When the lines in colors 1, 2, and 3 are extracted, 90°, 180°, and 270° are added to the angle acquired by the angle acquiring unit 430.

<A Flow of a Process of the First Embodiment>

Figure 20:
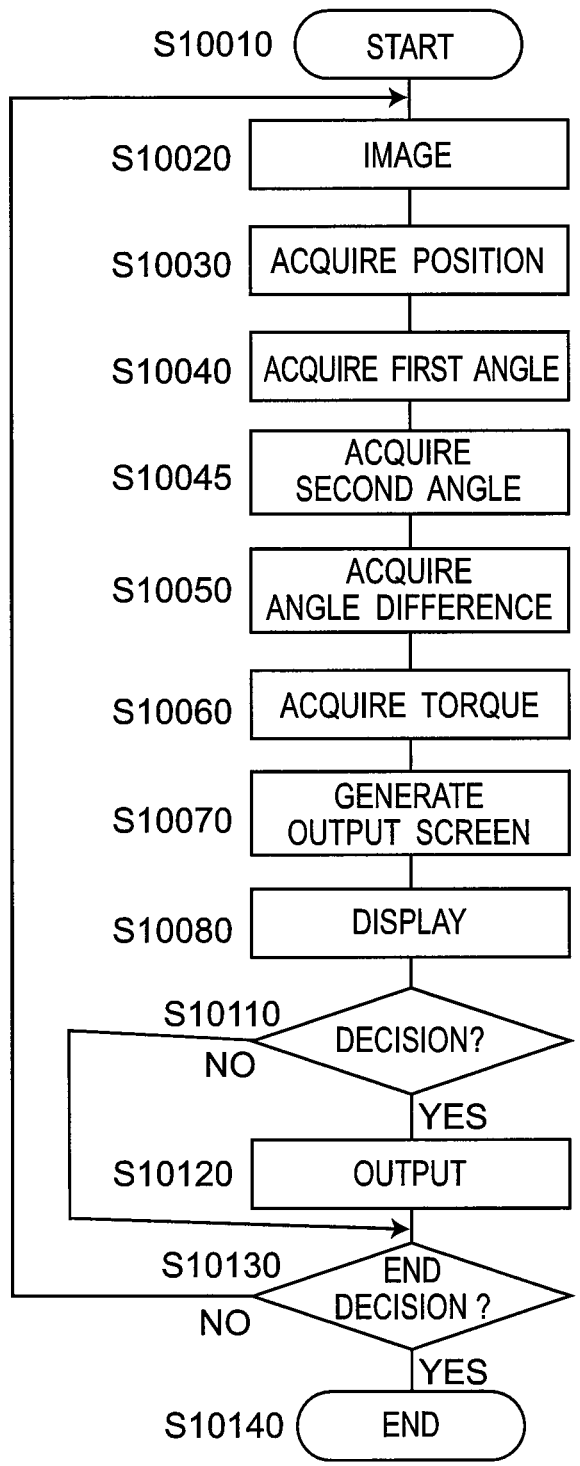
FIG. 20 is a flowchart showing a flow of a process according to the first embodiment.

A flow of a torque acquiring process of the first embodiment will be described with reference to a flowchart in FIG. 20.

Firstly, in step S10010, the torque measurement apparatus 1 starts the torque acquiring process.

Next, in step S10020, the imaging unit 31 and the first and second X-ray detection units 21 and 22 acquire images.

Next, in step S10030, the position acquiring unit 410 performs the position acquiring process of the position acquiring unit 410. That is, the position acquiring unit 410 acquires a position of the line 110 of the first linear body 10 in the image imaged by the imaging unit 31.

Next, in step S10040, the first angle acquiring unit 430 performs the angle acquiring process of the first angle acquiring unit 430. That is, the first angle acquiring unit 430 acquires a rotational angle of the line 110 in the range imaged by the imaging unit 31.

Next, in step S10045, the second angle acquiring unit 4200 performs the process of the first angle acquiring unit 430. That is, from the images imaged by the X-ray detection units 21 and 22, the second angle acquiring unit 4200 acquires a rotational angle of the curved portion 1020 at the distal end of the first linear body 10.

Next, in step S10050, the angle difference acquiring unit 450 performs the angle difference acquiring process of the angle difference acquiring unit 450. That is, the angle difference acquiring unit 450 acquires a difference between the rotational angle of the line 110 in the range imaged by the imaging unit 31 and the rotational angle of the curved portion 1020 at the distal end of the first linear body 10.

Next, in step S10060, the first torque calculation unit 460 performs the torque acquiring process based on the data of the torque holding unit 480. That is, the first torque calculation unit 460 sets, as a torque, a value acquired by multiplying the angle difference acquired by the angle difference acquiring unit 450 and the insertion length acquired by the insertion length acquiring unit 60 by a predetermined constant.

Next, in step S10070, the output screen generation unit 490 performs the output screen generating process of the output screen generation unit 490. That is, the output screen generation unit 490 generates a screen displaying the torque value acquired by the first torque calculation unit 460 and held by the torque holding unit 480.

Next, in step S10080, the display unit 51 performs the displaying process of the display unit 51. That is, the display unit 51 displays the screen generated by the output screen generation unit 490.

Next, in step S10110, the decision unit 4100 performs the deciding process of the decision unit 4100. That is, the decision unit 4100 decides whether or not an absolute value of the torque acquired by the torque acquiring unit 460 and held by the torque holding unit 480 is larger than the predetermined threshold value. When the decision unit 4100 decides that the absolute value of the torque is larger than the predetermined threshold value, the process is branched to step S10120. When the decision unit 4100 decides that the absolute value of the torque is not larger than the predetermined threshold value, the process is branched to step S10130.

In step S10120, the output unit 52 gives an alarm sound.

In step S10130, the torque measurement apparatus 1 performs end decision. Here, whether or not an end button, not shown, is pressed is decided and when the button is pressed, the process is branched to step S10140. When the button is not pressed, the process is branched to step S10020.

In step S10140, the torque measurement apparatus 1 ends the torque measuring process.

Here, for simplification, the second angle acquiring unit 4200 when the characteristic point is previously provided has been described. However, a second angle α may be acquired by the second angle acquiring unit 4200 based on a different pattern matching method.

<Catheter Inserting Operation>

An operator (serving as one example of a manipulator) manipulates the first linear body 10 to perform an operation. The operator inserts the first linear body 10 from the insertion opening 90a into a blood vessel. As an example, FIG. 9 is a view showing the distal end of the first linear body 10. The curved portion 1020 is provided at the distal end of the first linear body 10. The operator changes a direction of the curved portion 1020 according to operation condition in order to insert the catheter into the blood vessel or a body cavity with the curved portion 1020. In that case, the operator rotates the first linear body 10 in his/her hand to change the direction of the curved portion 1020.

However, when the curved portion 1020 is contacted with an occluded portion in the blood vessel, even when the first linear body 10 is rotated, the curved portion 1020 is not rotated, or the curved portion 1020 has a smaller rotational amount than the first linear body 10 or cannot be rotated. In such a case, a torque is generated in the first linear body 10. While the operator feels the torque with his/her hand, he/she determines whether he/she rotates the first linear body 10 more strongly or gives up rotation once. The determination is important because the blood vessel is damaged when the first linear body 10 is rotated to increase a load applied to the blood vessel.

<The Effect of the First Embodiment>

By using the torque measurement apparatus 1 according to the first embodiment, the operator can perform the task by checking the force applied to the first linear body 10 on the display unit 51. In addition, since the output unit 52 outputs the alarm sound, the operator can immediately notice that an excessive force is applied to the first linear body 10, thereby reducing the force applied to the first linear body 10. Further, when a skilled operator is performing the task, an unskilled operator can observe a value displayed on the display unit 51. The unskilled operator can thus learn how much torque he/she should use for the task. Furthermore, data held by the torque holding unit 480 when the skilled operator performs the task is compared with data held by the torque holding unit 480 when the unskilled operator performs the task. The task problems of the unskilled operator can thus be analyzed.

<Second Embodiment>

In the first embodiment, the first torque acquiring unit 40 acquiring a torque of the first linear body 10 made of a single material (or a configuration which is like the single material) and the torque measurement apparatus 1 have been described. In the second embodiment, the second torque acquiring unit 40a acquiring a torque of a second linear body 10a made of a plurality of materials and a torque measurement apparatus 1a will be described.

Figure 21:
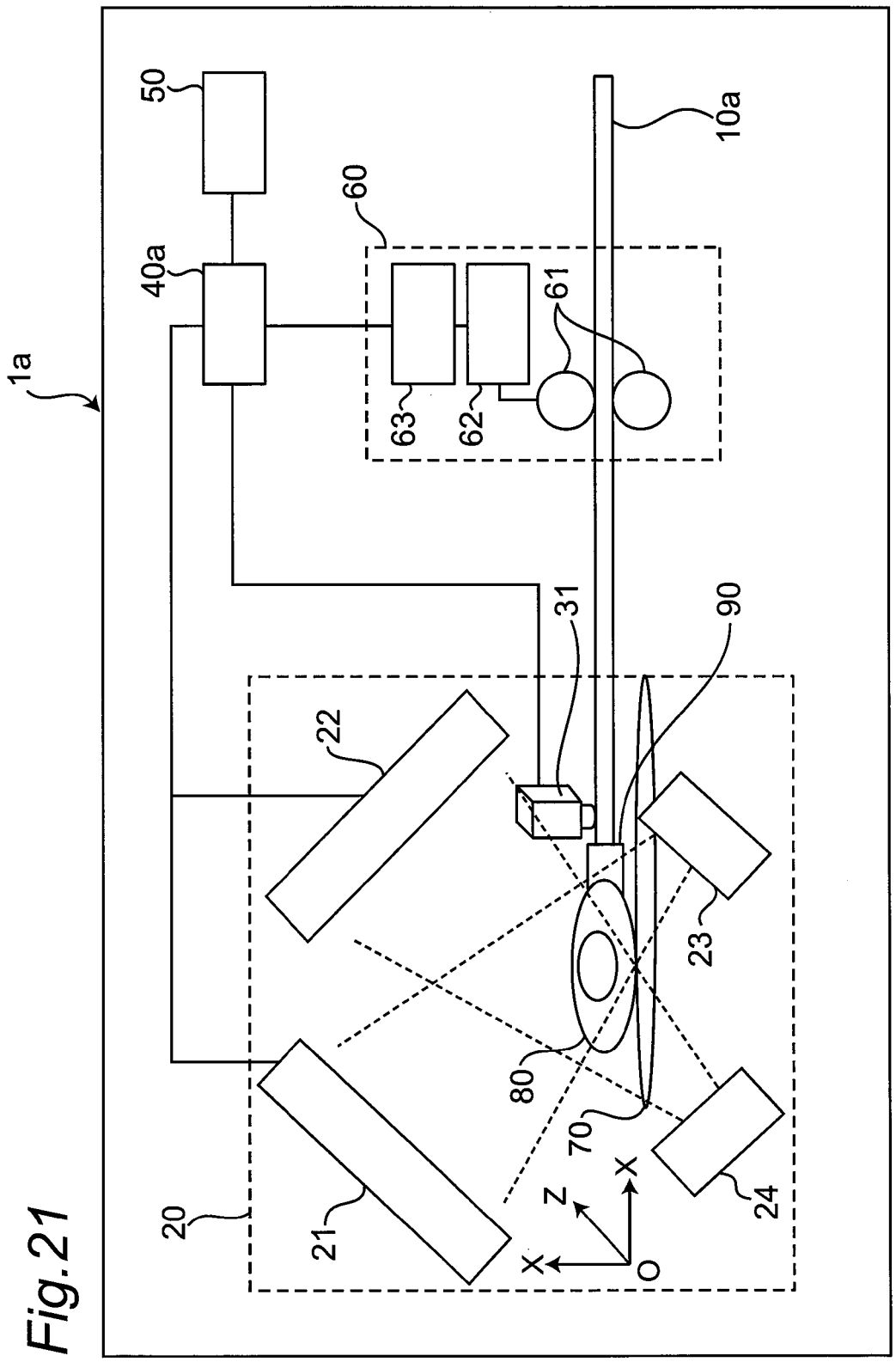
FIG. 21 is a view showing a configuration of a torque measurement apparatus according to a second embodiment.

FIG. 21 is a view showing a configuration of the torque measurement apparatus 1a of the second embodiment of the present invention. The torque measurement apparatus 1a has the second linear body 10a instead of the first linear body 10 according to the first embodiment, and a second torque acquiring unit 40a instead of the first torque acquiring unit 40 of the torque measurement apparatus 1. Other units are the same as the first embodiment, and the description is omitted.

The second linear body 10a is made of a plurality of materials. For instance, a portion at a distance of 50 mm from a distal end of the second linear body 10a is made of a flexible first material, and a portion thereafter is made of a second material harder than the first material.

Figure 22:
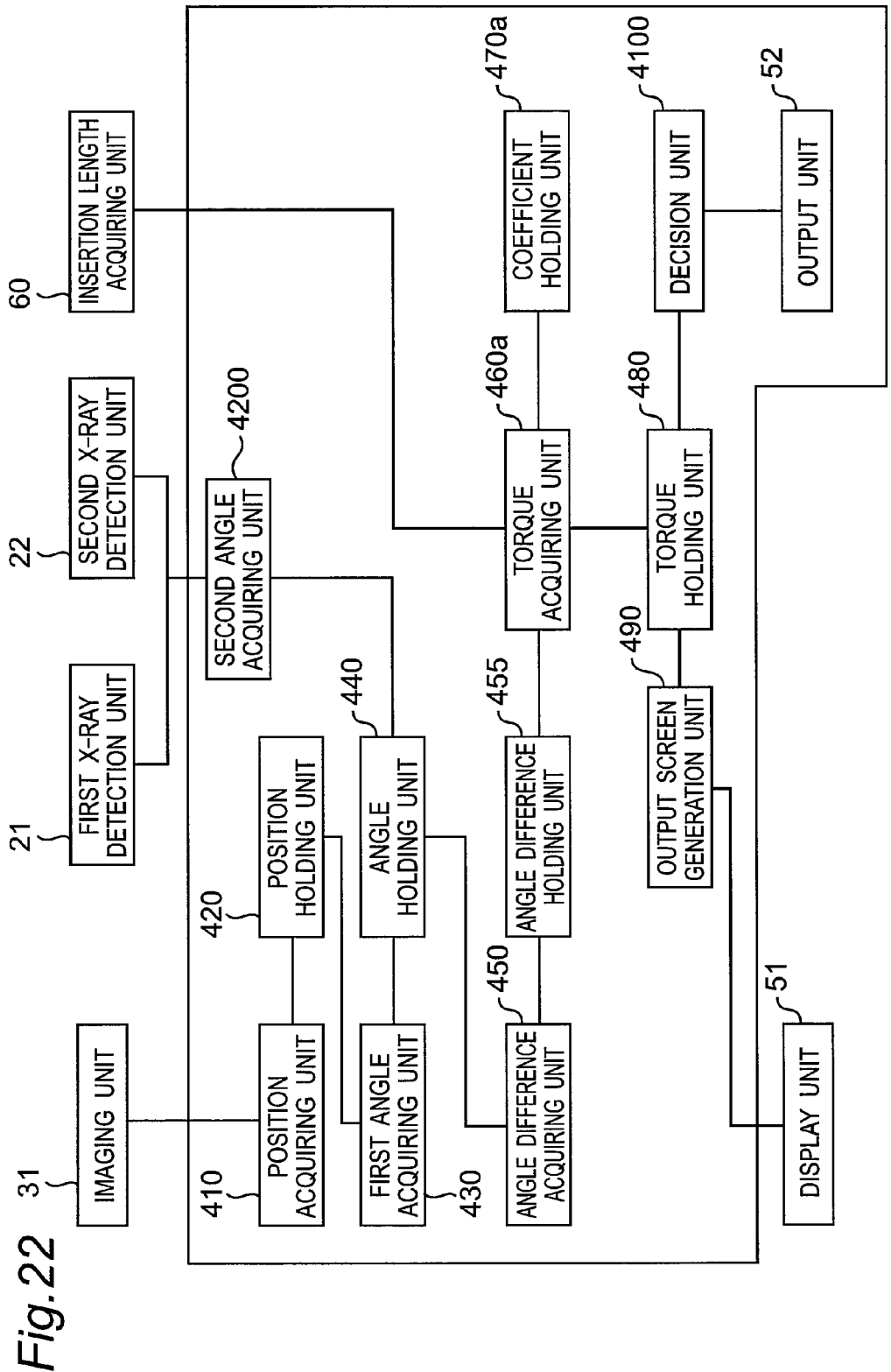
FIG. 22 is a view showing a configuration of a second torque acquiring unit according to the second embodiment.

FIG. 22 is a view showing a configuration of the second torque acquiring unit 40a. The second torque acquiring unit 40a has a second torque calculation unit 460a and a second coefficient holding unit 470a instead of the first torque calculation unit 460 and the first coefficient holding unit 470 of the first torque acquiring unit 40 of the first embodiment. Other units are the same as the first embodiment, and the description is omitted.

The second coefficient holding unit 470a holds a coefficient showing twistability of the second linear body 10a. In the first embodiment, a torque applied to the first linear body 10 made of a single material (or a material which can be like a single material) is expressed by Equation 13. However, here, a torque applied to the second linear body 10a made of a plurality of materials is calculated.

Figure 23:
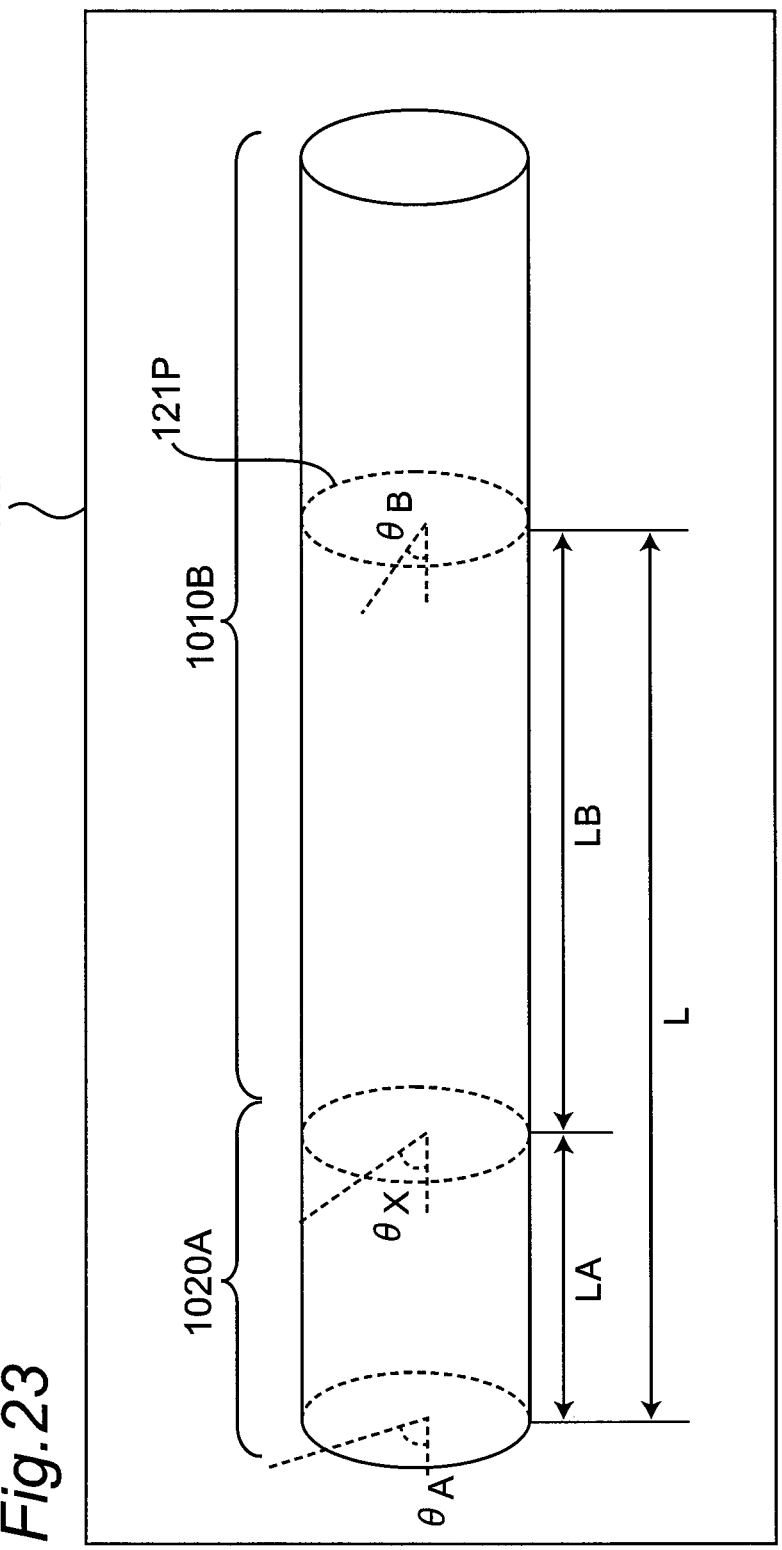
FIG. 23 is a view showing an example of a configuration of a second linear body according to the second embodiment.

FIG. 23 is a view showing the second linear body 10a. Referring to FIG. 23, a principle of measurement of a torque applied to the second linear body 10a will be described. A length of a curved portion (see the portion corresponding to the reference numeral 1020 in FIG. 9) at the distal end of the second linear body 10a is shorter than the entire length thereof. In FIG. 23, for simplifying the description, the curved portion is shown as a straight line in disregard of curve. Like the first linear body 10, although not shown, specifically, the second linear body 10a is formed on its surface with a linear characteristic portion parallel to the second linear body 10a in an axial direction (longitudinal direction). The second linear body 10a has a first portion 1020A located at the distal end and formed of a flexible first material, and a second portion 10103 connected to the first portion 1020A and formed of a second material harder than the first material. $G_1$ is a transverse elasticity modulus of the first portion 1020A, and $Ip_1$ is a polar moment of inertia of area thereof. $G_2$ is a transverse elasticity modulus of the second portion 1010B, and $Ip_2$ is a polar moment of inertia of area thereof.

The predetermined region 121 imaged by the imaging unit 31 is position 121P in FIG. 23. An angle $\theta_A$ is a rotational angle of the first portion 1020A at the distal end of the second linear body 10a acquired by the second angle acquiring unit 4200. An angle $\theta_B$ is a rotational angle of a characteristic portion of the second portion 1010B of the second linear body 10a in the predetermined region 121 acquired by the first angle acquiring unit 430. An angle $\theta_x$ is a rotational angle at a boundary portion between the first portion 1020A and the second portion 1010B.

A torque $T_1$ applied to the first portion 1020A is:

$$T_1 = G_1 \times Ip_1 \times (\theta_A - \theta_X)/LA \quad \text{(Equation 15)}.$$

In Equation 15, LA is a length of the first portion 1020A.
A torque $T_2$ applied to the second portion 1010B is:

$$T_2 = G_2 \times Ip_2 \times (\theta_X - \theta_B)/(L - LA) \quad \text{(Equation 16)}.$$

In Equation 16, L is a length from the distal end of the second linear body 10a to the predetermined region 121. That is, L is a length (insertion length) of the second linear body 10a (e.g., catheter) inserted into the insertion opening 90a of the sheath 90 acquired by the insertion length acquiring unit 60.

When the boundary portion between the first portion 1020A and the second portion 1010B is stopped or is moved at a constant speed, $T_1 = T_2$. Therefore, when $T_1 = T_2 = T$ and $\theta_A - \theta_B = \theta$, $$\theta = \left( \frac{1}{G_2 \times Ip_2} L + \frac{G_2 \times Ip_2 - G_1 \times Ip_1}{G_1 \times Ip_1 \times G_2 \times Ip_2} LA \right) T \quad \text{(Equation 17)}$$

is established. Here, even when the first portion 1020A and the second portion 1010B are actually moved, the first portion 1020A and the second portion 1010B are approximated by a state where the first portion 1020A and the second portion 10103 are stopped or moved at a constant speed. Then, the second torque acquiring unit 460a uses Equation 17 to calculate a force applied to the second linear body 10a.

When coefficients PC1 and PC2 are values of Equations 18 and 19, respectively, $$\frac{1}{G_2 \times Ip_2} PC1 =, \text{and} \quad \text{(Equation 18)}$$

$$\frac{G_2 \times Ip_2 - G_1 \times Ip_1}{G_1 \times Ip_1 \times G_2 \times Ip_2} PC2 = . \quad \text{(Equation 19)}$$

From Equations 18 and 19, Equation 17 is:

$$T = \frac{1}{PC1 \times L + PC2 \times LA} \theta. \quad \text{(Equation 20)}$$

The second coefficient holding unit 470a holds the coefficients PC1 and PC2, a value of length LA of the first portion 1020A, and a value of coefficient $P_0$.

Figure 24:
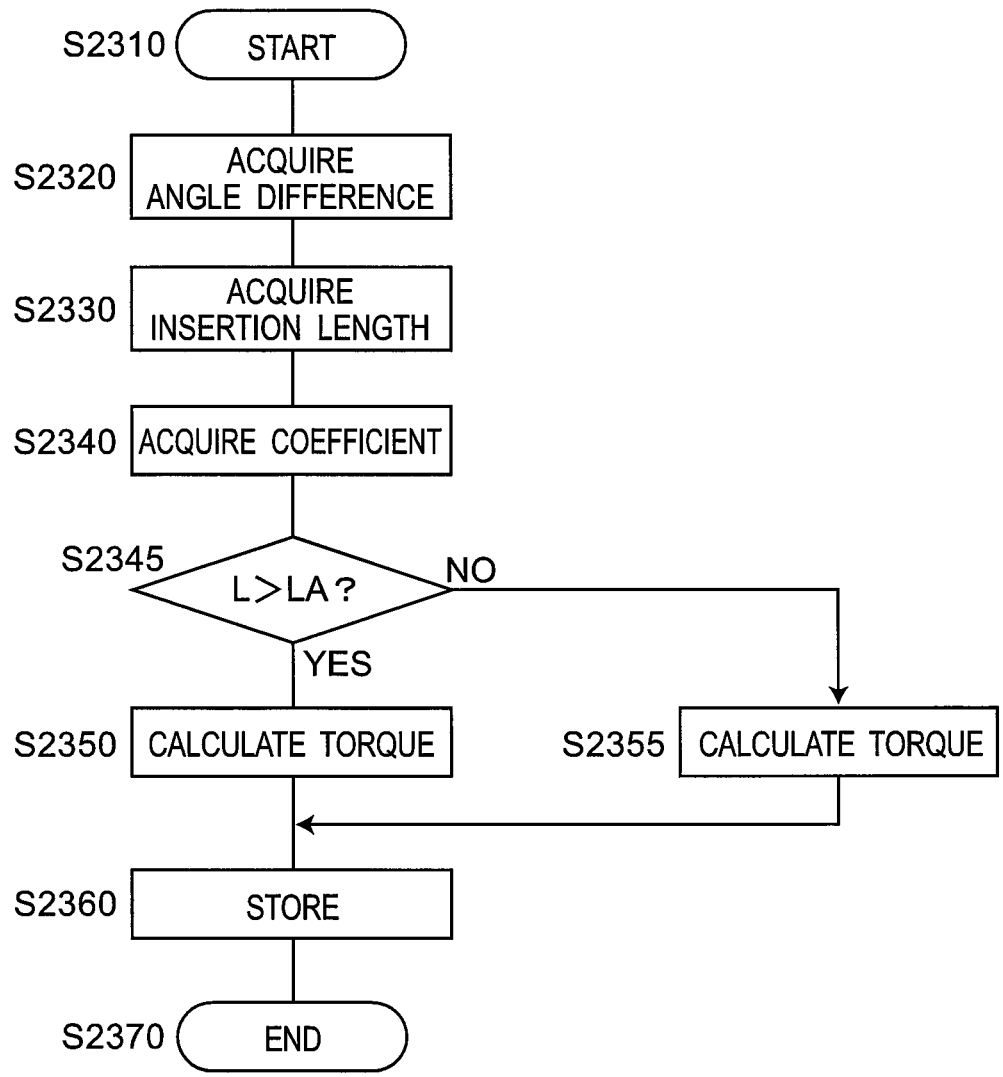
FIG. 24 is a flowchart showing a flow of a torque acquiring process of the second torque acquiring unit according to the second embodiment.

The second torque calculation unit 460a calculates a torque applied to the second linear body 10a based on Equation 20. FIG. 24 shows a flow of a torque acquiring process performed by the second torque calculation unit 460a.

Firstly, in step S2310, the second torque calculation unit 460a starts the torque acquiring process.

Next, in step S2320, the second torque calculation unit 460a acquires an angle difference θ from the angle difference holding unit 455.

Next, in step S2330, the second torque calculation unit 460a acquires an insertion length L from the insertion length acquiring unit 60.

Next, in step S2340, the second torque calculation unit 460a acquires coefficients PC1 and PC2, a length LA, and a coefficient $P_0$ from the second coefficient holding unit 470a.

Next, in step S2345, the second torque calculation unit 460a decides whether or not the length L is longer than the length LA. When the second torque calculation unit 460a decides that the length L is longer than the length LA, the process is branched to step S2350. When the second torque calculation unit 460a decides that the length L is not longer than the length LA, the process is branched to step S2355.

In step S2350, the second torque calculation unit 460a acquires a torque T. That is, the angle difference θ, the insertion length L, the coefficients PC1 and PC2, and the length LA, which are acquired in steps S2320 to S2340 are substituted into Equation 20, so that the second torque calculation unit 460a acquires the torque T.

In step S2355, the second torque calculation unit 460a obtains a torque T. That is, the angle difference θ, the insertion length L, and the coefficient $P_0$, which are obtained in steps S2320 to S2340 are substituted into Equation 13-2, so that the second torque calculation unit 460a obtains the torque T.

In step S2360, the second torque calculation unit 460a stores the torque T acquired in step S2350 or S2355 into the torque holding unit 480.

Next, in step S2370, the second torque calculation unit 460a ends the torque acquiring process.

<The Effect of the Second Embodiment>

By using the torque measurement apparatus 1a according to the second embodiment, the operator can perform the task while checking the force applied to the second linear body 10a made of the plurality of materials on the display unit 51. In addition, the output unit 52 outputs the alarm sound, so that the operator can immediately notice that an excessive force is applied to the second linear body 10a, thereby reducing the force. Further, when a skilled operator is performing the task, an unskilled operator can observe a value displayed on the display unit 51. The unskilled operator can thus learn how much torque he/she should use for the task. Furthermore, data held by the torque holding unit 480 when the skilled operator performs the task is compared with data held by the torque holding unit 480 when the unskilled operator performs the task. The task problems of the unskilled operator can thus be analyzed.

The second coefficient holding unit 470a holds the coefficient PC2 and the length LA, but may hold the product of the coefficient PC2 and the length LA.

<First Modification Example>

Figure 25:
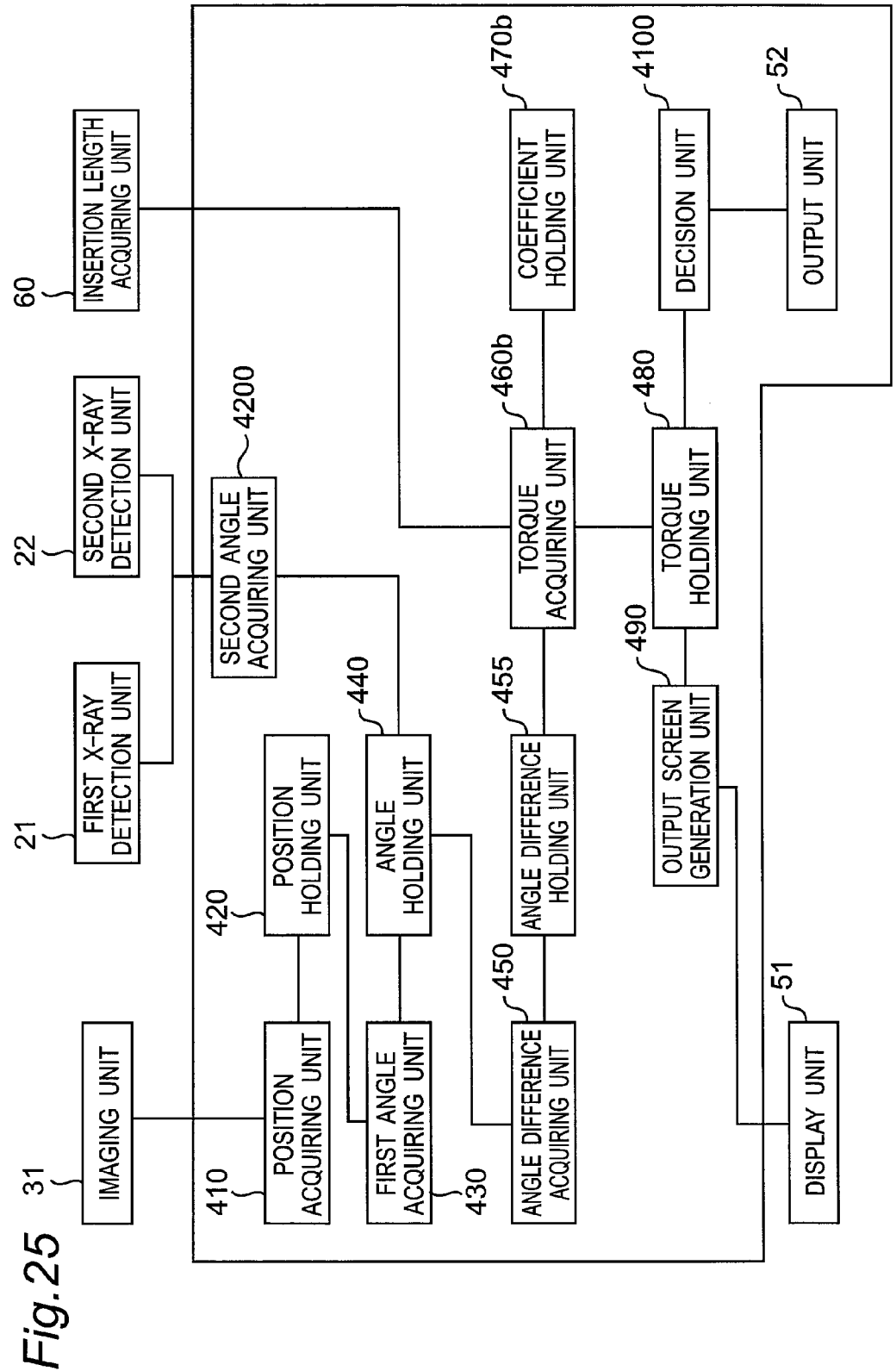
FIG. 25 is a view showing a configuration of a third torque acquiring unit according to a first modification example of the second embodiment.

In a first modification example of the second embodiment, a third torque acquiring unit 40b is used instead of the second torque acquiring unit 40a. FIG. 25 is a view showing a configuration of the third torque acquiring unit 40b. The third torque acquiring unit 40b has a third coefficient holding unit 470b and a third torque calculation unit 460b instead of the second coefficient holding unit 470a and the second torque calculation unit 460a.

The second coefficient holding unit 470a according to the second embodiment holds coefficients $P_0$, PC1, and PC2, and a length LA. The third coefficient holding unit 470b according to the first modification example holds a proportional constant f(L) of the angle difference θ and the torque T.

$$f(L) = G_1 \times IP_1/L \text{ (Here, } L \leq LA\text{)}$$

$$\frac{1}{PC1 \times L + PC2 \times LA} f(L) = \text{(Here, } L > LA\text{)}.$$

Equations 13 and 20 can be expressed by:

$$T = f(L) \times \theta (L \leq LA) \quad \text{(Equation 13-1), and}$$

$$T = f(L) \times \theta (L > LA) \quad \text{(Equation 20-1)}.$$

Figure 26:
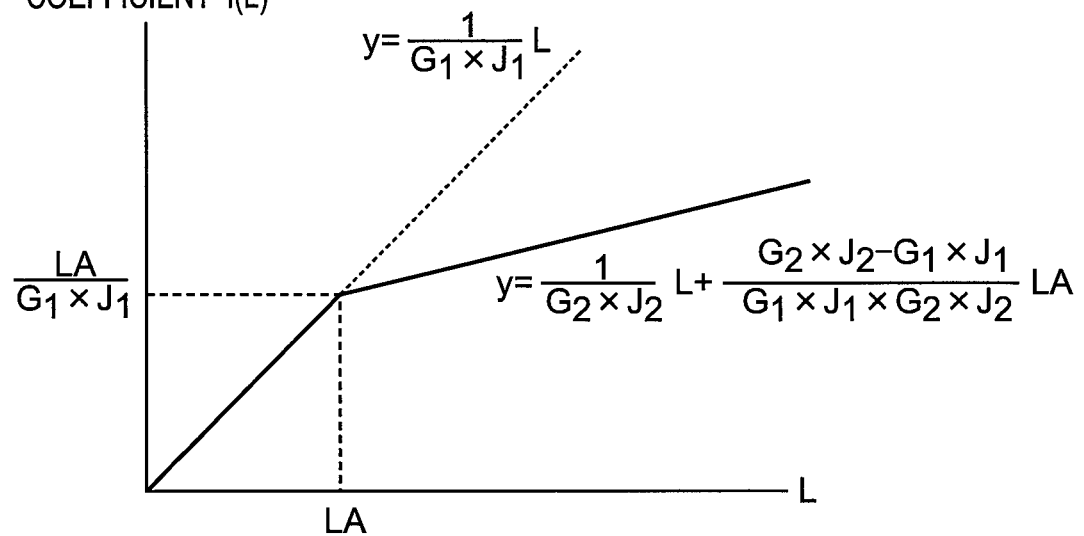
FIG. 26 is a graph showing a relation between an insertion length L and a proportional constant f(L) of an angle difference and a torque according to the first modification example of the second embodiment.

FIG. 26 is a graph showing a relation between the insertion length L and the proportional constant f(L) of the angle difference θ and the torque T. The horizontal axis shows the insertion length L, and the vertical axis is the proportional constant f(L). The third coefficient holding unit 470b holds the proportional constant f(L) with respect to a value of the insertion length L. For instance, the third coefficient holding unit 470b holds f(0), f(1), ..., f(300). FIG. 27 is a table-form view showing an example of a data structure held by the third coefficient holding unit 470b. In the table in FIG. 27, the first, second, ..., 301st rows hold the values of proportional constants f(L) when the insertion length is 0 mm, 1 mm, ..., 300 mm.

Figure 28:
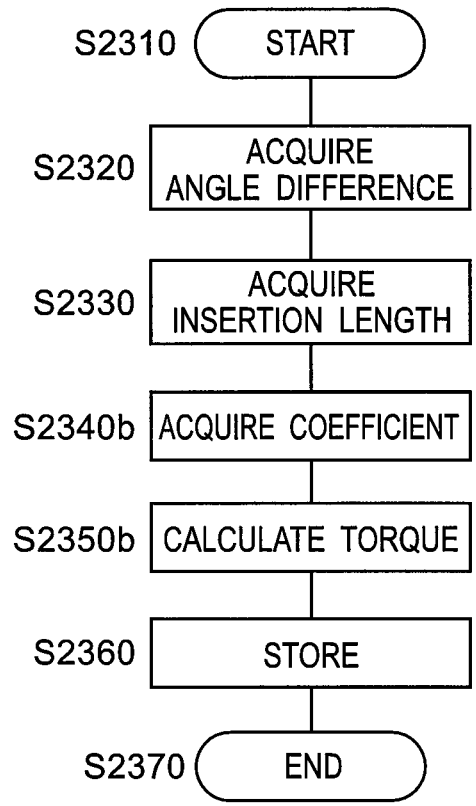
FIG. 28 is a flowchart showing a flow of a process of the third torque acquiring unit according to the first modification example of the second embodiment.
Figure 29:
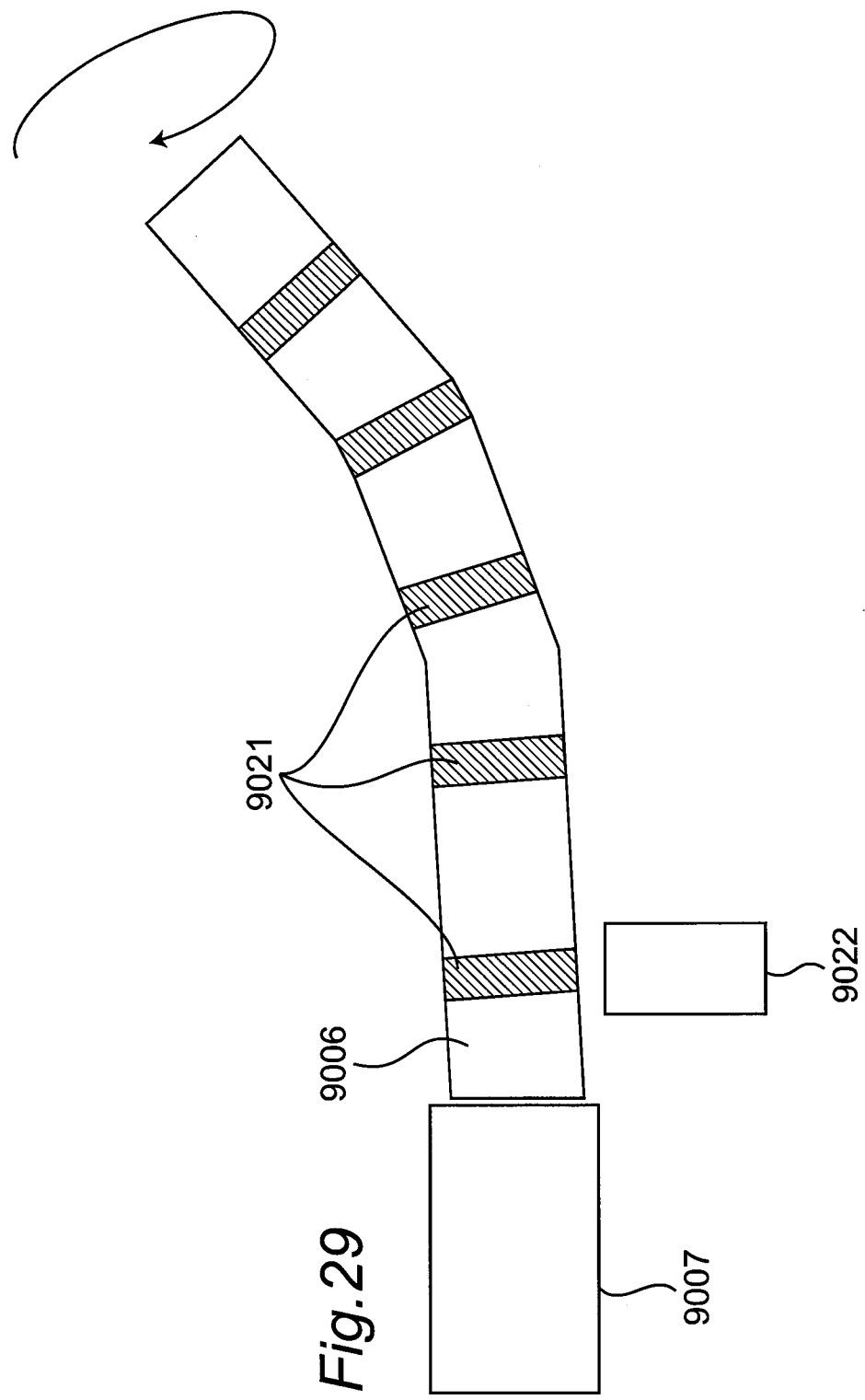
FIG. 29 is a view showing an overview of a torque measurement apparatus in Patent Literature 1.

FIG. 28 shows a flowchart of a torque acquiring process of the third torque calculation unit 460b. Steps other than steps S2340b and S2350b are the same as the steps having the same names in FIG. 24, and the description is omitted. Steps S2340b and S2350b will be described below.

In step S2340b, the third torque calculation unit 460b acquires a proportional constant f(L) from the third coefficient holding unit 470b. Here, L is an insertion length acquired by the insertion length acquiring unit 60. For instance, when the insertion length is 50 mm, the value of a proportional constant f(L) in the 51st column in FIG. 27 is acquired.

In step S2350b, the third torque calculation unit 460b calculates a torque T from the angle difference θ acquired in step S2320 and the proportional constant f(L) acquired in step S2340b. That is, the third torque calculation unit 460b sets θ×f(L) as the torque T.

According to the first modification example, a magnitude of a torque applied to the linear body made of the plurality of flexible materials can be acquired.

<Second modification example>

In the second embodiment, the coefficient (proportional coefficient) showing twistability of the linear body 10a is assumed to be known. On the contrary, in the second modification example, the torque measurement apparatus includes a coefficient acquiring device 2700 which acquires an unknown proportional coefficient of the linear body 10a having the unknown proportion coefficient.

Here, as described above, the coefficients are values determined according to the material of the first linear body 10, and are different. The first linear body 10 can thus be used in different instances. An example of using two guide wires A and B having different coefficients will be described below.

Figure 30:
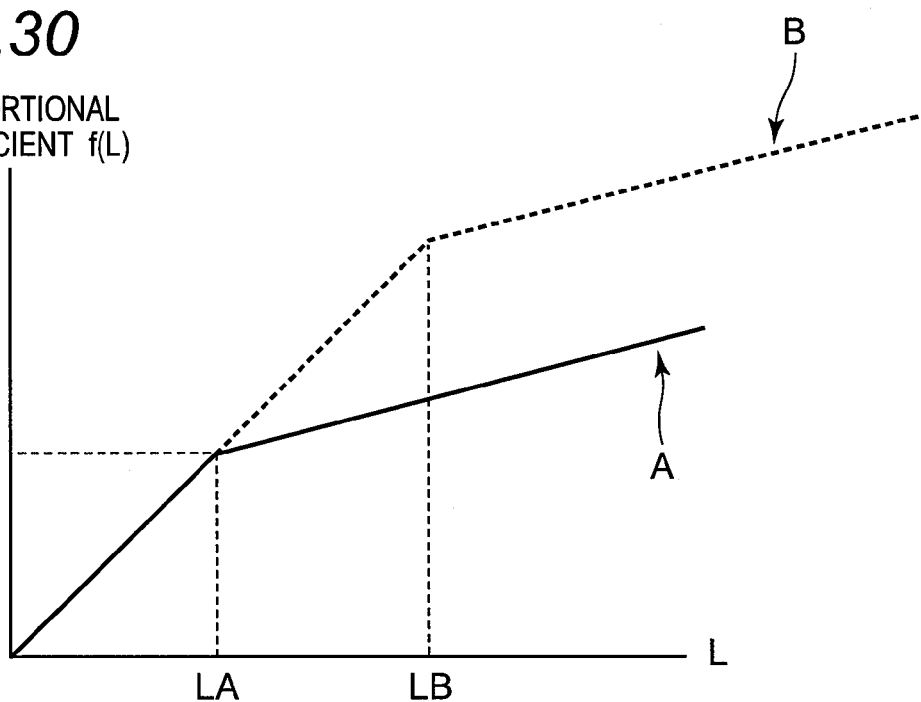
FIG. 30 is a graph showing proportional coefficients of two kinds of guide wires A and B according to a second modification example of the present invention.

FIG. 30 is a graph showing proportional coefficients of two kinds of guide wires A and B. A solid line represents the proportional coefficient of the guide wire A, and a dotted line represents the proportional coefficient of the guide wire B. The length LB in a soft portion at a distal end of the guide wire B is longer than the length LA in a soft portion at the distal end of the guide wire A. When the same force is applied to the guide wires A and B having the same insertion length L (L>LA), a rotational angle of the guide wire B is smaller since length LB in the soft portion at the distal end of the guide wire B is long, and a rotational angle of the guide wire A is larger.

Unless a large torque is applied to guide wire A, a large rotational angle cannot be acquired. The guide wire A is suitable when precise rotational angle adjustment is required.

The guide wire B can obtain a large rotational angle at a small torque. The guide wire B is thus suitable when a large rotational angle is required or when the operator desires to rotate the guide wire effectually. In addition, guide wire B is suitable for a doctor who can perform a detailed task.

In this way, since the use forms of the guide wires are different according to coefficient, it is important to acquire the coefficient in the second modification example.

Figure 31A:
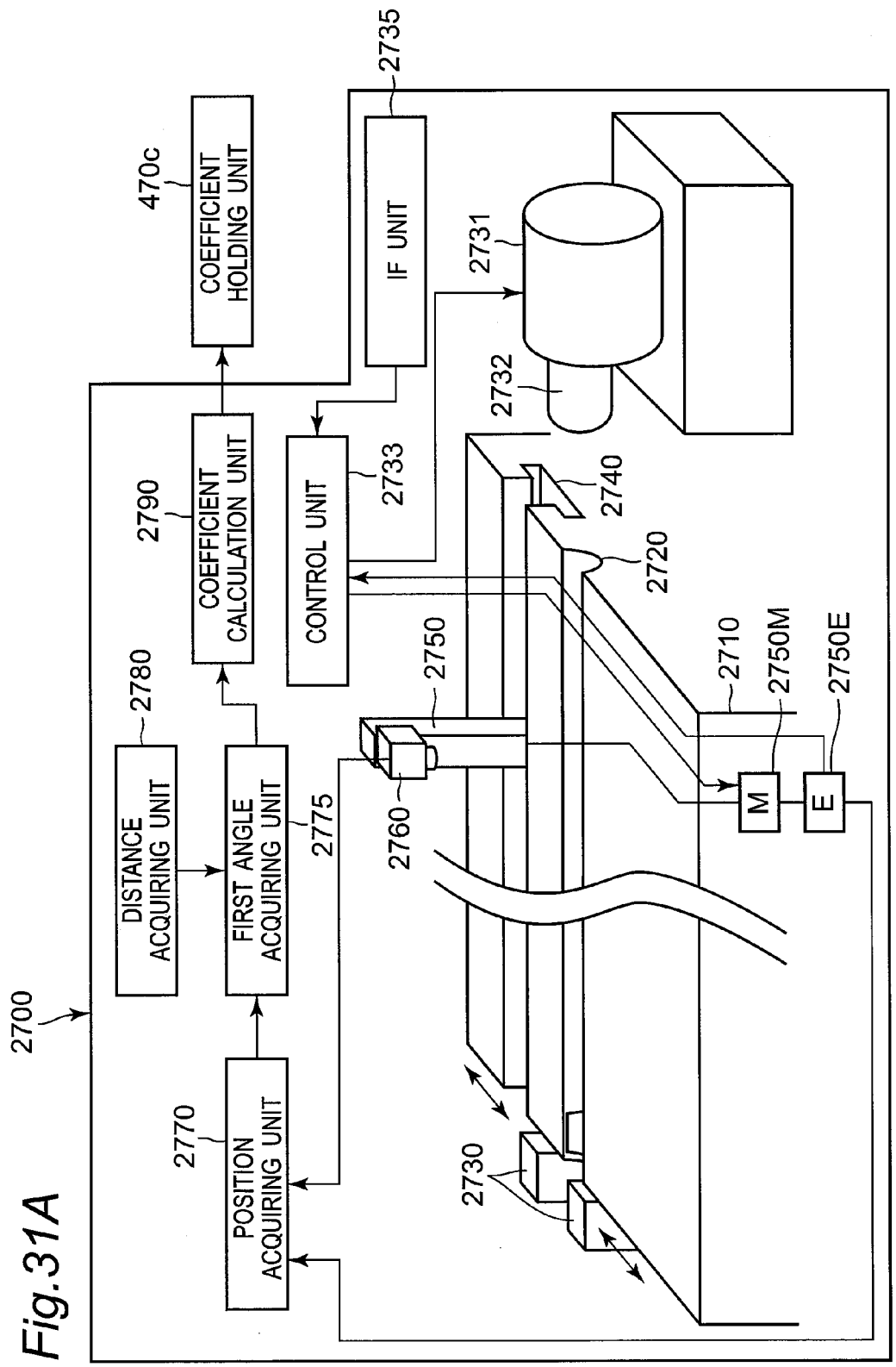
FIG. 31A is a view showing a configuration of a coefficient acquiring device of the second modification example.
Figure 31B:
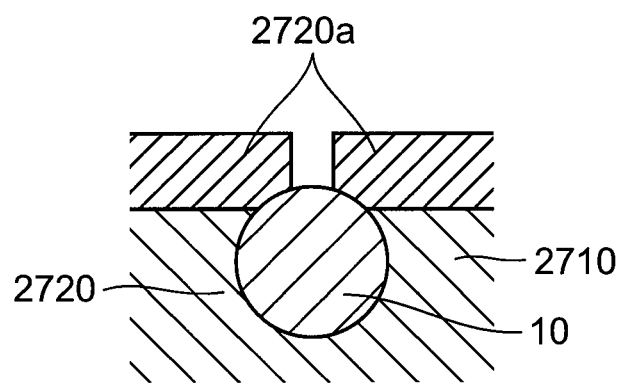
FIG. 31E is a cross-sectional view of a specific example of a groove of the coefficient acquiring device of the second modification example.

FIG. 31A is a view showing a configuration of the coefficient acquiring device 2700. FIG. 31B is a cross-sectional view of a specific example of a groove 2720. In a base 2710, provided are the groove 2720 through which the first linear body 10 is inserted and a rail 2740 on which a moving support 2750 is moved. The groove 2720 and the rail 2740 are parallel with each other. A fixing unit 2730 is provided at one end of the groove 2720. The fixing unit 2730 includes a chuck mechanism which can grip and fix one end of the first linear body 10. The fixing unit 2730 can be opened and closed in double-headed arrow directions to release or fix the one end of the first linear body 10.

As shown in FIG. 31B, as an example, the groove 2720 is formed along the shape of a circular cross section of the first linear body 10. An engaging cover 2720a is provided on an upper end side of the groove 2720 by narrowing a width of the groove 2720. The engaging cover 2720a engages the first linear body 10 not to remove the first linear body 10 from the groove 2720 when the first linear body 10 is given a later-described torque in the groove 2720 to be rotated. From a gap of the engaging cover 2720a, the line 110 of the first linear body 10 can be imaged by the imaging unit 2760. The coefficients of the first linear body 10 can thus be acquired more accurately.

As an example of a driving mechanism which automatically moves the moving support 2750 along the rail 2740 from one end of the base 2710 to the other end thereof, a stepping motor 2750M as an example of a driving device and an encoder 2750E which detects a rotational speed of the motor 2750M can be included. According to such a configuration, a later-described control unit 2733 drivingly controls the motor 2750M based on the rotational speed detected by the encoder 2750E to move the moving support 2750 along the rail 2740. Instead of automatically moving the moving support 2750 by the motor, the operator may manually move the moving support 2750 along the rail 2740. In that case, a scale is provided near the rail 2740, so that a moving distance of the moving support 2750 can be easily measured by the operator. A measurement value may be input from an IF unit 2735.

Figure 32:
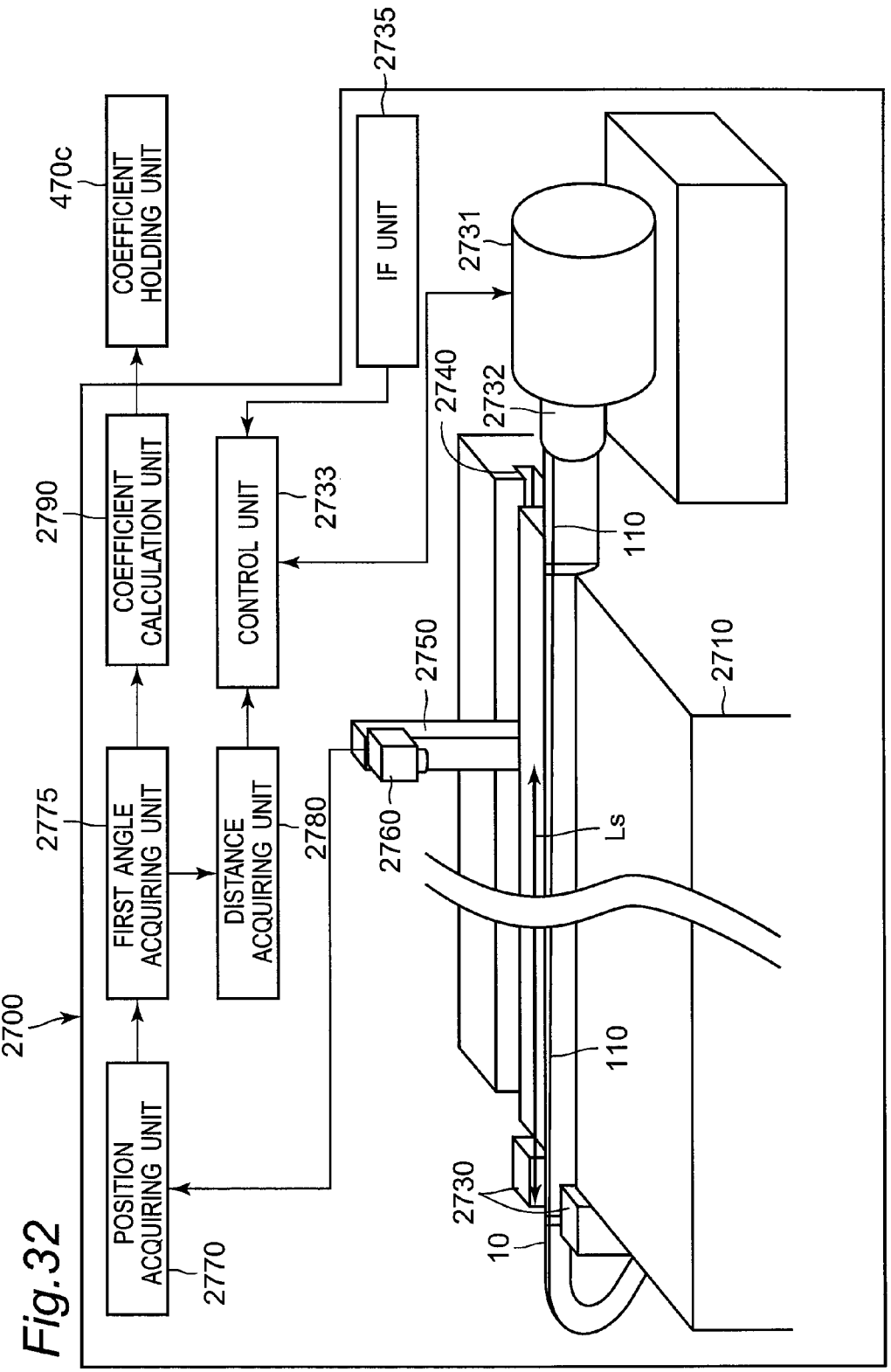
FIG. 32 is a view showing a state where a catheter which is an example of the first linear body is fixed in a fixing unit of the coefficient acquiring device of the second modification example.

FIG. 32 shows a state where the catheter 10 as an example of the first linear body is fixed to the fixing unit 2730. Like the first and second embodiments, the line 110 is provided on the surface of the first linear body 10.

A motor 2731 is arranged at one end on the side opposite to the fixing unit 2730 in the groove 2720. A rotational shaft of the motor 2731 has a chuck mechanism 2732 which can grip and fix the other end of the first linear body 10. Therefore, by opening or closing the chuck mechanism 2732 on the rotational shaft side, the other end of the first linear body 10 can be released or fixed.

The imaging unit 2760 is fixed to an upper portion of the moving support 2750.

The imaging unit 2760 is the same unit as the imaging unit 31 according to the first and second embodiments.

The coefficient acquiring device 2700 has a position acquiring unit 2770, a distance acquiring unit 2780, a first angle acquiring unit 2775, a coefficient calculation unit 2790, the control unit 2733, and the IF (interface) unit 2735.

The position acquiring unit 2770 acquires a position in which the line 110 is imaged based on the rotational speed detected by the encoder 2750E and the image imaged by the imaging unit 2760. The same process as the position acquiring unit 410 according to the first and second embodiments is performed.

The distance acquiring unit 2780 acquires a distance from one end of the catheter 10 gripped by the fixing unit 2730 to the moving support 2750 (e.g., a center of the imaged image of the imaging unit 2760). A length of the thick line in FIG. 32 shows a distance acquired by the distance acquiring unit 2780. Here, for simplification, an actual length of the curved portion at the distal end of the catheter 10 is ignored to measure a distance Ls of a flat portion other than the curved portion.

The first angle acquiring unit 2775 calculates a rotational angle θ of the linear body 10 in the position of the imaging unit 2760 from the position of the line 110 acquired by the position acquiring unit 2770. This is the same process as the first angle acquiring unit 430 according to the first and second embodiments.

The coefficient calculation unit 2790 uses Equation 21 to calculate a coefficient f(Ls) in a distance Ls from an angle θ acquired by the first angle acquiring unit 2770 at the time of applying a predetermined torque T to the chuck mechanism 2732 on the shaft side by the motor 2731. The coefficient calculation unit 2790 writes the acquired coefficient f(Ls) into a coefficient holding unit 470c.

$$f(Ls) = T/\theta \quad \text{(Equation 21)}$$

The IF (interface) unit 2735 is an interface which notifies completion of movement to the control unit 2733 when the operator moves the moving support 2750. For instance, the IF (interface) unit 2735 is a button or switch.

The control unit 2733 controls each unit of the coefficient acquiring device 2700.

<A Flow of a Coefficient Acquiring Process of the Coefficient Acquiring Device 2700>

FIG. 33 is a flowchart showing a flow of a coefficient acquiring process performed by the coefficient acquiring device 2700.

Firstly, as a pre-process, the operator allows both ends of the linear body 10 to be gripped by and fixed to the fixing unit 2730 and the chuck mechanism 2732 on the shaft side, and then moves the moving support 2750 to the left end (the catheter distal end).

In step 3210, the process of the coefficient acquiring device 2700 is started.

Next, in step 3220, the control unit 2733 drivingly controls the motor 2731 to produce a torque T in the rotational shaft having the chuck mechanism 2732. The driving control of the motor 2731 by the control unit 2733 can apply known driving control. For instance, the driving control of the motor 2731 can be performed based on the rotational speed detected by the encoder of the motor 2731.

Next, in step 3230, the position acquiring unit 2770 acquires a position of the line 110.

Next, in step 3240, the first angle acquiring unit 2775 calculates a rotational angle (first angle) θ of the linear body 10 in the position of the imaging unit 2760.

Next, in step 3250, the distance acquiring unit 2780 acquires a distance Ls from one end of the catheter 10 to the moving support 2750.

Next, in step 3260, the coefficient calculation unit 2790 calculates a coefficient f(Ls) to store the calculated coefficient into the coefficient holding unit 470c.

Next, in step 3270, the control unit 2733 stops the driving of the motor 2731.

Next, in step 3280, the operator moves the moving support 2750 e.g., in the right direction in FIG. 32 to stop movement, and notifies completion of movement to the control unit 2733 by using the IF unit 2735.

Next, in step 3290, the control unit 2733 determines whether or not the distance Ls acquired by the distance acquiring unit 2780 is a predetermined value A or larger. When the control unit 2733 decides that the distance Ls is the predetermined value A or larger, the process is ended in step 3300. The control unit 2733 decides that the distance Ls is not the predetermined value A or larger, the routine returns to step 3220. Here, predetermined value A is a value smaller than the distance from the fixing unit 2730 to the end of the base 2710.

In this way, the proportional coefficient acquiring process is performed from the distal end in the portion except for the curved portion of the catheter 10, at the least, to the region in which the catheter 10 enters into the body. The proportional coefficient acquiring process is performed, not only once, but also a plurality of times, to calculate an average value. The accuracy can thus be improved. In addition, based on the acquired proportional coefficient and position information, the coefficient holding unit 470c previously creates and holds information on a relation between the proportional coefficient and the position of the linear body, specifically, the graph in FIG. 30 or 26. Thus, the information held in the coefficient holding unit 470c can be effectively used in the second embodiment.

In a portion at a distance of e.g., approximately 30 cm from the distal end in the portion except for the curved portion of the catheter 10, whether the catheter 10 is bent well or not is often important. The proportional coefficient of the portion, that is, the coefficient showing twistability of the catheter 10, can be effectively acquired and used. In general, the catheter 10 is often manufactured of a plurality of materials, e.g., two materials. Due to the different materials, the proportional coefficient is changed halfway. The acquiring of the proportional coefficient greatly affects the accuracy at the time of performing the detailed task. It is thus important to acquire the proportional coefficient.

The motor 2731 is arranged on the base end of the catheter on the side opposite to the distal end thereof. The motor 2731 is not limited to this, and may be arranged at the distal end of the catheter to apply a torque from the distal end thereof.

<The Effect of the Second Modification Example>

According to the second modification example, the proportional coefficient of the linear body 10a having an unknown proportional coefficient can be acquired. In addition, by using the acquired proportional constant, a torque of the linear body 10a having an unknown proportional coefficient can be acquired by the torque measurement apparatus 1.

Though the present disclosure has been described above based on the above first to second embodiments and the first to second modification examples, the present disclosure should not be limited to the above-described first to second embodiments and the first to second modification examples. For example, the present disclosure also includes the following cases.

(1) In the description of the first and second embodiments, the examples of the flows of the processes are shown. However, the processes without any dependence relation may be replaced in the order, and may be executed at the same time.

(2) Part or all of the elements configuring first, second, or third torque acquiring unit 40, 40a, or 40b may be executed by a computer system that includes, for example, a microprocessor, ROM, RAM, hard disk unit, display unit, keyboard, mouse, and the like. A computer program is stored on the RAM or the hard disk unit. Functions of each part or element can be achieved by the microprocessor operating according to the computer program. The computer program mentioned here is a combination of a plurality of instruction codes that indicate commands to a computer for achieving predetermined functions.

(3) Part or all of the elements configuring the first, second, or third torque acquiring unit 40, 40a, or 40b may include one system LSI (Large Scale Integration) The system LSI is a super multifunction LSI manufactured by integrating a plurality of configuring units on one chip, specifically, a computer system including a microprocessor, ROM, RAM, and etc. The RAM stores a computer program. That is, the microprocessor is operated according to the computer program, so that the system LSI achieves its function.

(4) Part or all of the elements configuring the first, second, or third torque acquiring unit 40, 40a, or 40b may be formed by an IC card or a single module which can be removed from each apparatus. The IC card or the single module is a computer system including a microprocessor, ROM, RAM, and etc. The IC card or the single module may include a super multifunction LSI. That is, the microprocessor is operated according to the computer program, so that the IC card or the module achieves its function. Therefore, the IC card or the module may have tamper resistance. The software realizing the first, second, or third torque acquiring unit 40, 40a, or 40b according to the first or second embodiment or the first and second modification examples includes the following program. That is, this program is a torque measurement program of, when a linear body which has a linear characteristic portion in parallel with an axial direction thereof, is flexible, and has a curved portion at a distal end thereof is inserted through an insertion member into a body of a subject, measuring a torque applied to the linear body, the program which has a computer execute:

when the linear body includes a first portion located on a distal end side and formed of a first material and a second portion connected to the first portion and formed of a second material having hardness different from the first material, a first angle acquiring step of acquiring a rotational angle of the characteristic portion of the second portion in a predetermined region on an inlet side of the insertion member of the linear body extending through the insertion member by using a first angle acquiring unit;

a second angle acquiring step of acquiring a direction of the first portion of the linear body inserted into the body of the subject from an image of the linear body inserted into the body of the subject, and then, acquiring a rotational angle of the first portion of the linear body, by using a second angle acquiring unit; and a torque calculation step of calculating the torque based on a difference between the rotational angle of the second portion of the linear body acquired by the first angle acquiring unit and the rotational angle of the first portion of the linear body acquired by the second angle acquiring unit by using a torque calculation unit.

(5) Part or all of the elements configuring the first, second, or third torque acquiring unit 40, 40a, or 40b can also be realized as torque acquiring methods. In addition, by these methods, the present disclosure can be realized as a computer program which allows a computer to acquire a torque or digital signals including the computer program.

(6) In addition, it may be possible to execute the program by downloading it from a server or reading it from a predetermined storage medium (an optical disc such as a CD-ROM, a magnetic disc, a semiconductor memory, or the like). Part or all of the elements configuring the first, second, or third torque acquiring unit 40, 40a, or 40b may be realized by a computer-readable recording medium, such as a flexible disk, hard disk, CD-ROM, MO, DVD, DVD-ROM, DVD-RAM, Blu-ray Disc (BD), or semiconductor memory, on which the computer program or the digital signal is recorded. In addition, the present disclosure may be the digital signals recorded on these recording media.

(7) Part or all of the elements configuring the first, second, or third torque acquiring unit 40, 40a, or 40b can be realized as an electric communication line, a wireless communication line, a wire communication line, a network typified by the Internet, or the computer program or digital signals transmitted via data broadcast.

(8) Part or all of the elements configuring the first, second, or third torque acquiring unit 40, 40a, or 40b can be realized as a computer system including a microprocessor and a memory. In this case, the memory stores the computer program, and the microprocessor is operated according to the computer program.

(9) A different independent computer system may execute the processes of the present disclosure by recording the computer program or the digital signals into a recording medium to transfer the medium or by transferring the computer program or the digital signals via the network.

Further, one or more computers can be used to execute the program. That is, centralized processing or distributed processing can be performed.

In the previous description, the linear body includes the first portion located at the distal end and formed of the first material, and the second portion connected to the first portion and formed of the second material harder than the first material. However, there can be a reverse case. In brief, the linear body includes the first portion located at the distal end and formed of the first material, and the second portion connected to the first portion and formed of the second material having hardness different from the first material.

By properly combining the arbitrary embodiment(s) or modification example(s) of the aforementioned various embodiments and modification examples, the effects possessed by the embodiment(s) or modification examples) can be produced.

The entire disclosure of Japanese Patent Application No. 2012-129564 filed on Jun. 7, 2012, including specification, claims, drawings, and summary are incorporated herein by reference in its entirety.

The present disclosure is useful as the apparatus, method, and program measuring a torque applied to the flexible linear body. In addition, the present disclosure is useful as the apparatus, method, and program alarming an excessive torque applied to the linear body.

Although the present disclosure has been fully described in connection with the embodiments thereof with reference to the accompanying drawings, it is to be noted that various changes and modifications are apparent to those skilled in the art. Such changes and modifications are to be understood as included within the scope of the present disclosure as defined by the appended claims unless they depart therefrom.

What is claimed is:

1. A torque measurement apparatus for, when a linear body is inserted through an insertion member into a body of a subject, measuring a torque applied to the linear body around an axial direction of the linear body, the linear body having a linear characteristic portion in parallel with the axial direction of the linear body, the linear body being flexible, the linear body having a curved portion at a distal end of the linear body, the apparatus comprising:
a first angle acquiring unit which acquires a rotational angle of the linear characteristic portion in a predetermined region on an inlet side of the insertion member of the linear body extending through the insertion member;
a second angle acquiring unit which acquires a direction of the curved portion of the linear body inserted into the body of the subject from an image of the linear body inserted into the body of the subject, and then, acquires a rotational angle of the distal end of the linear body; and
a torque calculation unit which calculates the torque applied to the linear body around the axial direction of the linear body based on a difference between (i) the rotational angle of the linear characteristic portion in the predetermined region on the inlet side of the insertion member of the linear body extending through the insertion member acquired by the first angle acquiring unit and (ii) the rotational angle of the distal end of the linear body acquired by the second angle acquiring unit,
wherein the linear body includes a first portion located on a distal end side and formed of a first material and a second portion connected to the first portion and formed of a second material having hardness different from the first material,
the first angle acquiring unit acquires a rotational angle of the linear characteristic portion of the second portion of the liner body in the predetermined region on the inlet side of the insertion member of the linear body extending through the insertion member,
from an image of the linear body inserted into the body of the subject, the second angle acquiring unit acquires a rotational angle of the first portion of the linear body inserted into the body of the subject, and
the torque calculation unit calculates the torque applied to the linear body around the axial direction of the linear body based on a difference between (i) the rotational angle of the linear characteristic portion of the second portion of the linear body in the predetermined region on the inlet side of the insertion member of the linear body extending through the insertion member acquired by the first angle acquiring unit and (ii) the rotational angle of the first portion of the linear body inserted into the body of the subject acquired by the second angle acquiring unit.

2. The torque measurement apparatus according to claim 1, further comprising a coefficient acquiring device which acquires a proportional coefficient of the linear body based on difference between the materials of the linear body,
wherein the torque calculation unit calculates the torque applied to the linear body around the axial direction of the linear body in consideration of information on a relation between the coefficient which is previously created based on the coefficient acquired by the coefficient acquiring device and a position of the linear body.

3. The torque measurement apparatus according to claim 1, further comprising a transparent image acquiring unit which images a transparent image of the linear body inserted into the body of the subject,
   wherein from the transparent image acquired by the transparent image acquiring unit, the second angle acquiring unit acquires the direction of the curved portion of the linear body inserted into the body of the subject to acquire the rotational angle of the distal end of the linear body.

4. The torque measurement apparatus according to claim 1, further comprising:
   a camera which images the predetermined region on the inlet side of the insertion member of the linear body extending through the insertion member; and
   a position acquiring unit which acquires a position of the linear characteristic portion in the predetermined region on the inlet side of the insertion member of the linear body extending through the insertion member based on the image imaged by the camera,
   wherein the first angle acquiring unit acquires the rotational angle of the linear characteristic portion in the predetermined region on the inlet side of the insertion member of the linear body extending through the insertion member based on the position of the linear characteristic portion in the predetermined region on the inlet side of the insertion member of the linear body extending through the insertion member acquired by the position acquiring unit.

5. The torque measurement apparatus according to claim 1, further comprising:
   a decision unit which decides whether or not the torque applied to the linear body around the axial direction of the linear body acquired by the torque calculation unit is larger than a predetermined value; and
   an output unit which outputs an alarm when the decision unit decides that the torque applied to the linear body around the axial direction of the linear body is larger than the predetermined value.

6. A torque measurement apparatus for, when a linear body is inserted through an insertion member into a body of a subject, measuring a torque applied to the linear body around an axial direction of the linear body, the linear body having a linear characteristic portion in parallel with the axial direction of the linear body, the linear body being flexible, the linear body having a curved portion at a distal end of the linear body, the apparatus comprises:
   a first angle acquiring unit which acquires a rotational angle of the linear characteristic portion in a predetermined region on an inlet side of the insertion member of the linear body extending through the insertion member;
   a second angle acquiring unit which acquires a direction of the curved portion of the linear body inserted into the body of the subject from an image of the linear body inserted into the body of the subject, and then, acquires a rotational angle of the distal end of the linear body; and
   a torque calculation unit which calculates the torque applied to the linear body around the axial direction of the linear body based on a difference between (i) the rotational angle of the linear characteristic portion in the predetermined region on the inlet side of the insertion member of the linear body extending through the insertion member acquired by the first angle acquiring unit and (ii) the rotational angle of the distal end of the linear body acquired by the second angle acquiring unit,
   wherein the linear body includes a first portion located on an distal end side and formed of a first material and a second portion connected to the first portion and formed of a second material harder than the first material,
   the first angle acquiring unit acquires a rotational angle of the linear characteristic portion of the second portion of the linear body in the predetermined region on the inlet side of the insertion member of the linear body extending through the insertion member,
   from an image of the linear body inserted into the body of the subject, the second angle acquiring unit acquires a rotational angle of the first portion of the linear body inserted into the body of the subject, and
   the torque calculation unit calculates the torque applied to the linear body around the axial direction of the linear body based on a difference between (i) the rotational angle of the linear characteristic portion of the second portion of the linear body acquired by the first angle acquiring unit and (ii) the rotational angle of the first portion of the linear body inserted into the body of the subject acquired by the second angle acquiring unit.

7. A torque measurement method of, when a linear body is inserted through an insertion member into a body of a subject, measuring a torque applied to the linear body around an axial direction of the linear body, the linear body having a linear characteristic portion in parallel with the axial direction of the linear body, the linear body being flexible, the linear body having a curved portion at a distal end of the linear body, the linear body including a first portion located on a distal end side and formed of a first material and a second portion connected to the first portion and formed of a second material having hardness different from the first material, the method comprising:
   acquiring a rotational angle of the linear characteristic portion of the second portion of the linear body in a predetermined region on an inlet side of the insertion member of the linear body extending through the insertion member by using a first angle acquiring unit;
   acquiring a direction of the first portion of the linear body inserted into the body of the subject from an image of the linear body inserted into the body of the subject, and then, acquiring a rotational angle of the first portion of the linear body inserted into the body of the subject, by using a second angle acquiring unit; and
   calculating, by using a torque calculation unit, the torque applied to the linear body around the axial direction of the linear body based on a difference between (i) the rotational angle of the linear characteristic portion of the second portion of the linear body in the predetermined region on the inlet side of the insertion member of the linear body extending through the insertion member acquired by the first angle acquiring unit and (ii) the rotational angle of the first portion of the linear body inserted into the body of the subject acquired by the second angle acquiring unit.

8. A non-transitory computer-readable recording medium having stored thereon a torque measurement program for, when a linear body is inserted through an insertion member into a body of a subject, measuring a torque applied to the linear body around an axial direction of the linear body, the linear body having a linear characteristic portion in parallel with the axial direction of the linear body, the linear body being flexible, the linear body having a curved portion at a distal end of the linear body, the linear body including a first portion located on a distal end side and formed of a first material and a second portion connected to the first portion and formed of a second material having hardness different from the first material, the program causing a computer to execute:
- acquiring a rotational angle of the linear characteristic portion of the second portion in a predetermined region on an inlet side of the insertion member of the linear body extending through the insertion member by using a first angle acquiring unit;
- acquiring a direction of the first portion of the linear body inserted into the body of the subject from an image of the linear body inserted into the body of the subject, and then, acquiring a rotational angle of the first portion of the linear body inserted into the body of the subject, by using a second angle acquiring unit; and
- calculating, by using a torque calculation unit, the torque applied to the linear body around the axial direction of the linear body based on a difference between (i) the rotational angle of the linear characteristic portion of the second portion of the linear body in the predetermined region on the inlet side of the insertion member of the linear body acquired by the first angle acquiring unit and (ii) the rotational angle of the first portion of the linear body inserted into the body of the subject acquired by the second angle acquiring unit.

* * * * *